(12) United States Patent
Cleveland

(10) Patent No.: US 9,386,921 B2
(45) Date of Patent: Jul. 12, 2016

(54) SYSTEMS AND METHODS FOR MINIATURIZING EYETRACKING SYSTEMS

(71) Applicant: LC Technologies, Inc., Fairfax, VA (US)

(72) Inventor: Dixon Cleveland, Annandale, VA (US)

(73) Assignee: LC Technologies, Inc., Fairfax, VA (US)

( * ) Notice: Subject to any disclaimer, the term of this patent is extended or adjusted under 35 U.S.C. 154(b) by 0 days.

(21) Appl. No.: 14/634,751

(22) Filed: Feb. 28, 2015

(65) Prior Publication Data

US 2015/0238079 A1 Aug. 27, 2015

Related U.S. Application Data

(63) Continuation of application No. 14/634,410, filed on Feb. 27, 2015.

(60) Provisional application No. 61/945,551, filed on Feb. 27, 2014, provisional application No. 61/945,546, filed on Feb. 27, 2014.

(51) Int. Cl.
*G03B 29/00* (2006.01)
*A61B 3/14* (2006.01)
*A61B 3/113* (2006.01)
*A61B 3/00* (2006.01)
(Continued)

(52) U.S. Cl.
CPC ............... *A61B 3/113* (2013.01); *A61B 3/0025* (2013.01); *A61B 3/145* (2013.01); *B81B 7/008* (2013.01); *B81B 7/02* (2013.01); *G02B 27/0093* (2013.01); *G03B 9/02* (2013.01); *G03B 15/03* (2013.01); *G03B 15/05* (2013.01); *G03B 15/06* (2013.01); *G03B 15/16* (2013.01); *G03B 17/561* (2013.01); *G06F 3/013* (2013.01); *G06K 9/00597* (2013.01); *G06K 9/46* (2013.01); *G06T 7/0042* (2013.01); *H04N 5/23212* (2013.01); *H04N 5/23219* (2013.01); *G03B 17/17* (2013.01); *G06T 2207/30041* (2013.01)

(58) Field of Classification Search
USPC .............................................. 396/51, 199, 18
See application file for complete search history.

(56) References Cited

U.S. PATENT DOCUMENTS

| 4,974,010 A * | 11/1990 | Cleveland | A61B 3/113 351/210 |
| 2005/0013021 A1* | 1/2005 | Takahashi | G02B 17/0642 359/837 |
| 2013/0314303 A1* | 11/2013 | Osterhout | G06F 3/005 345/8 |

*Primary Examiner* — Clayton E Laballe
*Assistant Examiner* — Warren K Fenwick
(74) *Attorney, Agent, or Firm* — John R. Kasha; Kelly L. Kasha; Kasha Law LLC

(57) ABSTRACT

A miniature eye tracking system is disclosed that includes a camera, a microelectromechanical (MEMS) device, and a processor. The camera images an eye. The MEMS device controls the view-direction of the camera. The processor receives an image of the eye from the camera, determines the location of the eye within the camera image, and controls the MEMS to keep the camera pointed at the eye. In another embodiment, the MEMS device controls an adjustable focus of the camera. The processor determines the focus condition of the eye image, and controls the MEMS device to maintain a desired focus condition of the camera on the eye. In another embodiment, the MEMS device controls an adjustable camera zoom. The processor determines the size of the eye image within the overall camera image, and controls the MEMS to maintain a desired size of the eye image within the overall camera image.

5 Claims, 18 Drawing Sheets

(51) Int. Cl.
*B81B 7/02* (2006.01)
*B81B 7/00* (2006.01)
*H04N 5/232* (2006.01)
*G03B 9/02* (2006.01)
*G03B 15/03* (2006.01)
*G03B 15/06* (2006.01)
*G03B 15/05* (2006.01)
*G03B 15/16* (2006.01)
*G03B 17/56* (2006.01)
*G06F 3/01* (2006.01)
*G06K 9/00* (2006.01)
*G06K 9/46* (2006.01)
*G06T 7/00* (2006.01)
*G02B 27/00* (2006.01)
*G03B 17/17* (2006.01)

| IMAGES OF A POINT LIGHT SOURCE ON THE CAMERA SENSOR SURFACE | APERTURE TYPE | |
|---|---|---|
| CAMERA FOCUS CONDITION | ASYMMETRIC | SYMMETRIC |
| TOO NEAR UNIVERTED APERTURE IMAGE | ☢ | ◯ |
| IN FOCUS | ○ | ○ |
| TOO FAR INVERTED APERTURE IMAGE | ☢ | ◯ |

SYSTEMS AND METHODS FOR MINIATURIZING EYETRACKING SYSTEMS

CROSS-REFERENCE TO RELATED APPLICATION

This application is a continuation of U.S. patent application Ser. No. 14/634,410, filed Feb. 27, 2015 and entitled "Improved Asymmetric Aperture for Eyetracking," which claims the benefit of U.S. Provisional Patent Application No. 61/945,551, filed Feb. 27, 2014, and U.S. Provisional Patent Application No. 61/945,546, filed Feb. 27, 2014. The content of all of the above is incorporated by reference herein in their entireties.

INTRODUCTION

The present invention relates to systems for determining the focus condition of a lens, controlling the focus of the lens, finding a range to an object, and reducing the size of eyegaze tracking or eye tracking devices. Note that the terms "eyegaze tracking" and "eye tracking" are used interchangeably throughout this application.

The terms eye tracking and eyegaze tracking include, but are not limited to: recognizing an eye and features of an eye within an image, the features of the eye including, including, for example, the pupil, iris, sclera, eyelids, canthi, and corneal reflection(s) of light(s) projected onto the eye; measuring the coordinate location and image dimensions of an eye and its features within an image; computing the locations of the physical eye and its features in 3-dimensional space, where the eye's spatial computations are derived from the eye image measurements; computing the angular orientation of an eye in space, based, for example, on the relative locations of the eye features; computing the gaze line of an eye in space, e.g. the central visual line of the eye that originates at the center of the foveola on the retina, passes through the primary nodal point of the eye, and projects out of the eye into space in accordance with the location and orientation of the eye in space; and computing the location of the gaze point of an eye in space, e.g. the point in space where the gaze line intercepts a physical object that the eye sees, i.e. the location in space of the object that projects its image onto the foveola of the eye's retina.

In many imaging applications, it is often desired to focus a lens or other collector on an object and to maintain the lens sharply focused despite the object's longitudinal motion, i.e., motion along the optical axis of the lens. One such imaging application is eye tracking in which an apparatus determines the point in space at which the eye is looking. In eye tracking, precise knowledge of the eye's 3D location in space is generally required in order to measure the eye's gazepoint in space, and measuring the longitudinal range, herein designated Z, from the camera to the eye is an essential element of measuring the eye location.

Prior eye trackers are disclosed in U.S. Pat. No. 3,864,030 to Cornsweet; U.S. Pat. Nos. 4,287,410 and 4,373,787 to Crane et al.; U.S. Pat. No. 4,648,052 to Friedman et al.; and in certain U.S. patent applications of Thomas E. Hutchinson, Ser. Nos. 07/086,809; 07/267,266, filed Nov. 4, 1988; and Ser. No. 07/326,787. Those systems typically illuminate the eye with infrared light which is reflected from various parts of the eye, particularly the cornea and retina, to an imaging device such as a video camera. The spatial relations between the reflections are used to determine the gaze point. For example, the corneal reflection moves about eighty micrometers per degree of eye rotation with respect to the pupil reflection.

From elementary geometry, it will be appreciated that the location finding accuracy of such trackers is heavily dependent on accurately locating the three-dimensional (3D) coordinates of the eye reflections with respect to the apparatus and with respect to each other. Thus, the gazepoint accuracy can be improved by improving the measurement of the range Z from the camera to the eye and maintaining the camera sharply focused on the eye. (To complete the full 3D location of the eye within the camera frame of reference, the lateral X,Y coordinates are typically measured from the x,y location of the eye image within the camera's overall 2D image.)

One (uncomfortable) way of keeping the camera focused is by preventing relative motion of the eye and camera, e.g., by restraining the eye or head of the user. Another way is by providing an autofocus mechanism to the camera. (If lateral X,Y motions of the eye, i.e., motions perpendicular to the optical axis, exceed the camera's instantaneous field of view, a lateral tracking mechanism is also needed.) The above-cited U.S. patents describe two types of autofocus mechanism whereby longitudinal eye displacements (along the Z axis) are detected using the corneal reflection of a light source. In the patent to Cornsweet, a variable amplitude modulation due to motion of the source's image formed between two chopper wheels is detected. In the patents to Crane et al., the difference in output between two detectors longitudinally equidistant, when properly focused, from the source's image is detected. U.S. Pat. No. 3,869,694 to Merchant et al. describes an improved eyegaze tracker that includes an ultrasonic position measuring system that is used to adjust the focus of the tracker.

Other devices for focusing an imaging device on an eye are disclosed in U.S. Pat. No. 4,251,139 to Matsumura; U.S. Pat. No. 4,626,089 to Takahashi et al.; U.S. Pat. No. 4,673,264 to Takahashi; and U.S. Pat. No. 4,678,297 to Ishikawa et al. The patents to Ishikawa et al. and Matsumura disclose optical system focusing and alignment by projecting a mark image onto the cornea and detecting the reflected mark image. The patents to Takahashi et al. and Takahashi disclose projecting a mark image into the eye and detecting the mark image reflected from the retina.

Those devices and other mechanisms such as multi-camera-parallax devices are unsuitable for many gaze trackers and other applications because they typically require additional equipment and complex calibration, and may not provide the required range measurement accuracy. In addition, they can excessively restrict the freedom of motion of the user.

Some video eye trackers (illustrated in FIG. 3 for example) estimate the range to the eye by using multiple, widely separated illumination sources (320) to produce multiple corneal reflections within the camera's eye images. They then use the distance(s) between those multiple corneal reflection images to estimate the range from the eye from the camera. As the range to the eye increases, the distance between the corneal reflections within the eye image decreases in inverse proportion to the range, thus providing information needed to estimate the range. One key disadvantage of the widely-separated illuminator approach to measuring the range to the eye is that the width of the overall eye tracking apparatus must be large in order to accommodate the illuminator separation. An advantage of the asymmetric aperture method is that it allows the precise measurement of eye range without the use of widely separated illuminators, thereby reducing the overall size of the eye tracker apparatus. A second key disadvantage of the widely separated illuminators is that it depends on knowledge of the anatomical properties of the particular eye being tracked. It must know both the radius of the eye's corneal surface and the flattening properties of the corneal surface toward its outer edges. The asymmetric aperture method discussed here does not depend on this individual eye information. The range measurement accuracy of the asymmetric aperture method depends only on the optical quality of the camera lens and aperture, both of which are under full control of the eye tracker designer.

U.S. Pat. No. 4,974,010 to Cleveland et al. discloses a focus analysis system comprising a) a point source whose focus condition is to be measured, b) a camera including a lens, an asymmetric aperture with a noncircular shape of distinguishable orientation and a sensor for capturing the image formed by the lens the aperture, and c) an image processor that analyzes the captured image and determines the focus condition of the point light source based on the point source's image as shaped by the asymmetric aperture. This focus analysis system is particularly useful in video eye trackers because the reflection of the eye tracker's illuminator off the corneal surface of the user's eye, commonly called the corneal reflection, is a virtual point light source that is precisely tied to the location of the eye in space. Thus measuring the focus condition and range to the corneal reflection is equivalent to measuring the focus condition and range to the eye itself. This focus analysis system provides the required range measurement accuracy for many gaze or eye trackers, without restricting the freedom of motion of users.

A key aspect of U.S. Pat. No. 4,974,010 to Cleveland is the shape of the camera's asymmetric aperture that admits light to the sensor. As is well known in the camera art, a typical lens aperture is circular in its perimeter shape. There are several reasons for this circular perimeter shape. A) It is the easiest shape to manufacture. B) The circular perimeter is generally considered optimum from an optics perspective in that a circle provides a maximum area (and thus allows the aperture to capture a maximum amount of light) with respect to a minimum lateral extent of the aperture area. C) The circular shape maximizes the image depth of field and minimizes the image focus blur resulting from the finite aperture size required to capture the numbers of photons necessary to generate a usable image.

The conventional circular aperture shape, however, does not imbue sufficient information into the camera image to be able to determine the focus condition of an object being viewed. While the magnitude of an object's focus blur does provide useful information as to the magnitude of how far out of focus an object is, the blur from a circular aperture provides no information about the direction of whether the camera is focused too far or too near. The purpose of designing an optimum asymmetric aperture is to maximize the ability of the image processor to measure both the direction and magnitude of the focus condition accurately.

In camera optics, a lens "aperture" typically refers to the size, shape and position of the optical opening that allows light from the outside world to pass through the lens and reach the camera sensor. Since an aperture opening is transparent, the opening itself typically contains no physical material, and the size, shape and position of the opening are physically implemented by the construction of opaque material positioned around the opening. For purposes of this discussion, an aperture "device" refers to the mechanical components of the surrounding opaque material used to configure the aperture "opening".

FIGS. 1A and 1B illustrate examples of an asymmetric and a symmetric aperture (each including both the aperture openings and the aperture devices), along with images of a point light source on the camera sensor surface given (prior art). FIG. 1A illustrates an example of an asymmetric aperture. FIG. 1B illustrates a circular example of a symmetric aperture. FIG. 1C is a table illustrating the shapes of the images of a point light source given: a) an asymmetric versus a symmetric aperture, and b) the lens being focused too near versus too far. Note that the opaque portions 102 and 112 of the aperture devices in FIGS. 1A and 1B are shaded, and the transparent aperture openings 101 and 111 are shown in white. In all subsequent aperture drawings, the opaque portion of the aperture, e.g., the aperture device, are depicted in white, not shaded.

The shape of one asymmetric aperture 100 whose image from a point light source can be analyzed using the Cleveland method is shown in FIG. 1A. For comparison purposes, a conventional, symmetric, circular aperture 110 is shown in FIG. 1B. The table in FIG. 1C illustrates the shapes of the images of a point light source given: a) an asymmetric versus a symmetric aperture, and b) the lens being focused too near versus too far. From this table it can be seen that the shapes of the inverted (lens focused too far) and the non-inverted (lens focused too near) images of the point light source are distinguishable for the asymmetric aperture but indistinguishable for the symmetric aperture. Thus, with the asymmetric aperture, it is possible to determine not only the magnitude of how far out of focus the lens is, but also the polarity (near versus far) of the focus error.

Note: The definitions of "symmetric" versus "asymmetric" apertures in the context of measuring a lens's focus condition are clear from FIGS. 1A and 1B. If the inverted shape of the aperture is indistinguishable from the uninverted shape, the aperture is symmetric, and provides no information regarding the near-vs-far polarity of the focus condition. If the inverted and non-inverted shapes are distinguishable, the shape is asymmetric.

The particular "pie slice" shapes of the transparent openings 101 of the asymmetric aperture of FIG. 1A are constructed such that the inverted and uninverted images of the overall aperture pattern are maximally different; i.e., when the overall centers of mass of the inverted and uninverted images are spatially aligned with one another, the individual transparent-opening regions of the two patterns are maximally opposite. With the exception of the central region discussed later, transparent regions on one pattern correspond to opaque regions on the other. This maximal pattern difference maximizes the detectability of the inverted vs non-inverted feature of the image, thus increasing the image processor's ability to resolve the focus condition when the camera is in its desired state of being well focused.

Though the small details of the shape of the transparent openings may affect the image processing function's precise ability to resolve fine differences in the lens focus condition, it is obvious to one skilled in the art that the more general shapes of the asymmetric aperture patterns discussed here provide the basic ability to measure focus condition and maximize light utilization, and that minor variations in the exact perimeter shapes of the transparent openings do not circumvent these inventions.

Note that the asymmetric aperture of FIG. 1A is opaque at the center. (As discussed later and shown in FIG. 5, the center is opaque because an on-axis illuminator (not shown) is located there.) One drawback of this "closed-center" asymmetric aperture design is that it blocks a large, central portion of the camera lens, thus blocking a large percentage of the light reaching the camera sensing means, and underutilizing the most optically useful center portion of the lens.

It is also well known in the camera art that the center of the aperture is typically aligned with the center of the camera lens to minimize the size (i.e., diameter) of the lens required to make full use of the available aperture.

In contrast to the circular design of typical camera apertures, the asymmetric aperture method noted in U.S. Pat. No. 4,974,010 to Cleveland utilizes non-symmetric aperture shapes to generate image features that convey focus-condition information about objects the camera is viewing. Also as noted above, when designing asymmetric apertures there is a tradeoff between image depth of field and focus condition information.

It is also well known in the video eye tracking art that the level of illumination the eye tracker apparatus projects onto the eye must be sufficient to produce a high quality image of the eye. Light emitting diodes (LEDs) are often used to provide this illumination.

Reducing the size of eye tracking devices is critical to meet emerging needs for incorporating eye trackers into small computer devices, particularly handheld devices such as smart phones. During typical usage, handheld devices move considerably with respect to a person's head, so maintaining a sufficiently high quality image of the user's eye(s) to measure his gaze accurately is a difficult challenge. One way to obtain such high quality eye images is to utilize telephoto lenses fitted with motorized gimbal mechanisms to keep the eye tracker camera pointed at and focused on the user's eye(s). In this discussion, motorized gimbal mechanisms in eye tracking devices are called eyefollowers, where eyefollower gimbals can include camera pan/tilt drives, camera autofocusing mechanisms, and camera zoom controls. Currently, the motorized gimbal mechanisms of eyefollowers are too large, heavy and expensive to be built into handheld devices where it would be desirable to incorporate eye trackers.

BRIEF DESCRIPTION OF THE DRAWINGS

The skilled artisan will understand that the drawings, described below, are for illustration purposes only. The drawings are not intended to limit the scope of the present teachings in any way.

Figures 1A, 1B, 1C:
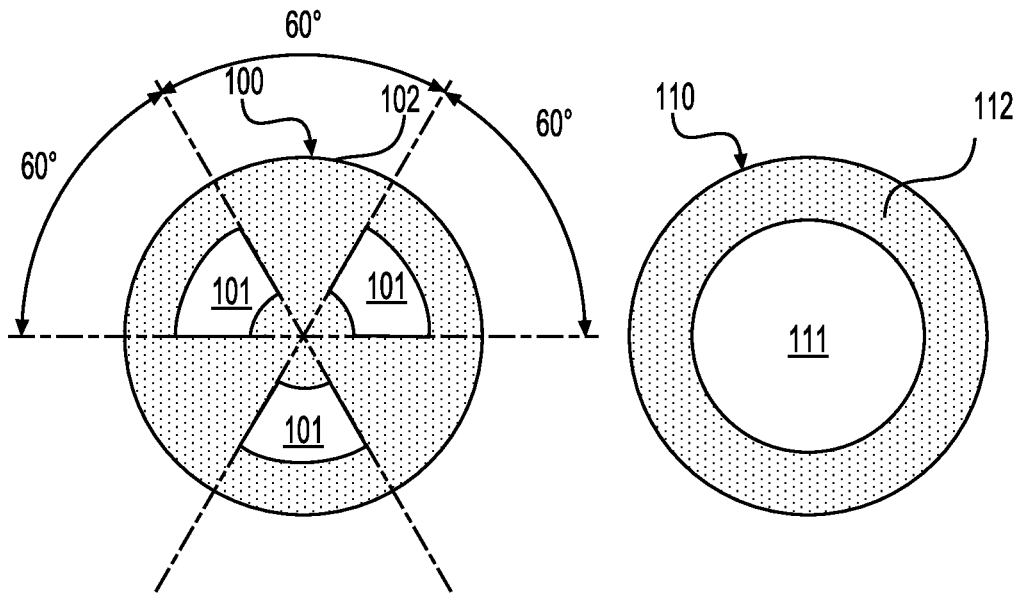
FIGS. 1A and 1B illustrate examples of an asymmetric and a symmetric aperture (each including both the aperture openings and the aperture devices), along with images of a point light source on the camera sensor surface given (prior art).
FIG. 1C illustrates the shapes of the images of a point light source given: a) an asymmetric versus a symmetric aperture, and b) the lens being focused too near versus too far.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DESCRIPTION OF VARIOUS EMBODIMENTS

Eye Tracker

In general, an eye tracker or eye gaze tracker is a device that is used to determine where an eye is looking. Modern eye trackers, sometimes referred to as video eye trackers, are camera-based devices that observe a person's eyes and predict the point in space where the person is looking. This point in space is referred to as the gazepoint, for example. The line connecting the fovea of the eye, the center of the eye pupil, and the gazepoint is referred to as the gaze line, for example.

Figure 2:
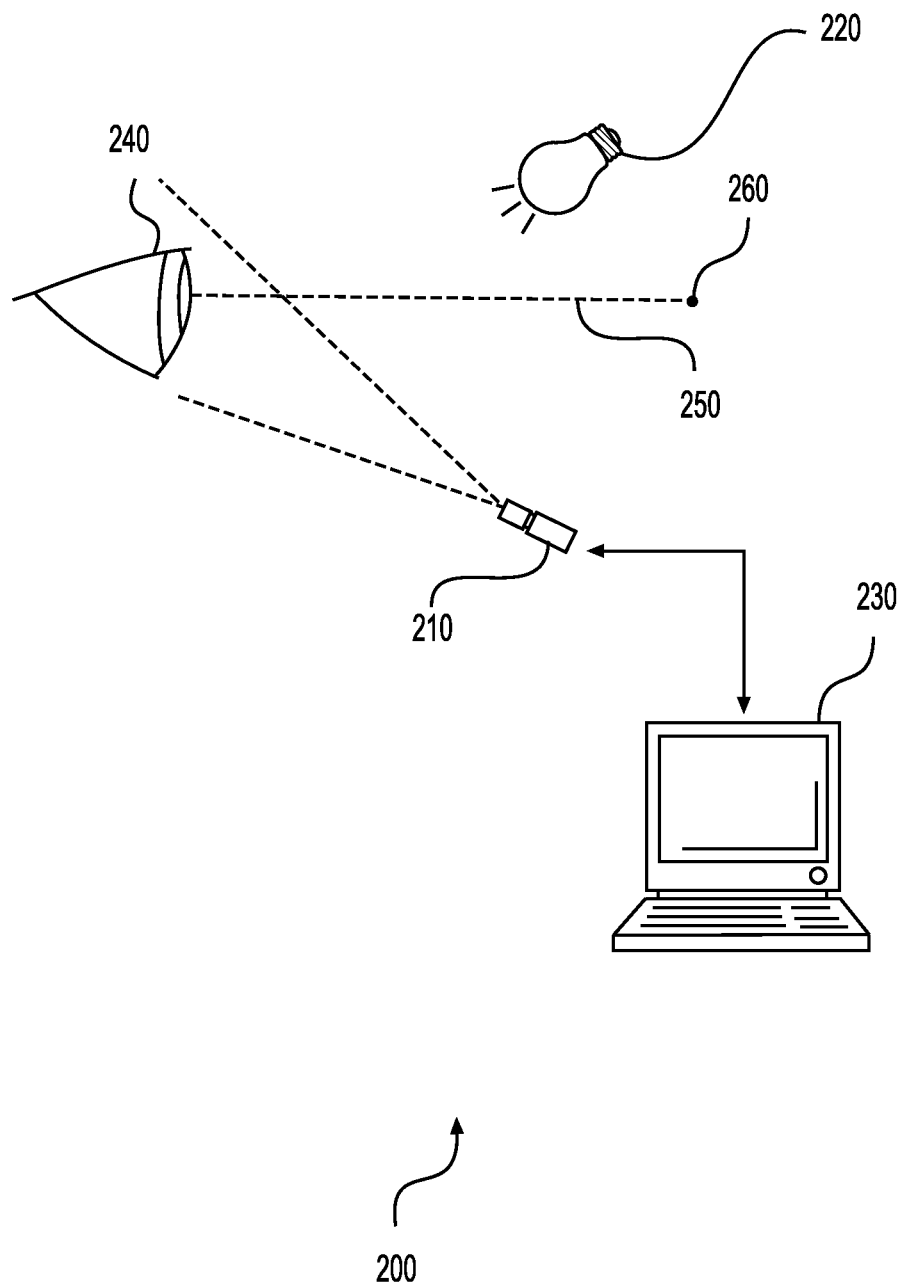
FIG. 2 is a schematic diagram showing an eye tracker with a single illuminator (prior art).

FIG. 2 is a schematic diagram showing a typical eye tracker 200 without a gimbal (prior art). Eye tracker 200 includes image detector or camera 210, light source 220, and processor 230. Light source 220 illuminates eye 240, and camera 210 images eye 240. Processor 230 receives the image from camera 210 and determines from the image a) the camera's focus condition of the eye and b) the orientation and position of eye 240 in space. Based on the position and focus condition of the eye within the camera image, the processor is able to compute the 3-dimensional location and orientation of actual eye 240 within the camera body frame of reference. From the eye's 3-dimensional location and orientation in space, the processor is able to compute the eye's gaze line 250 and gazepoint 260 in space.

Eye tracker 200 can include additional elements. For example, eye tracker 100 can include one or more additional cameras (not shown) or one or more additional optical devices (not shown) to determine the range from camera 210 to eye 240. Eye tracker 200 can also include a display (not shown) to determine the gazepoint in an image displayed by processor 230 on the display.

Also, in FIG. 2 image detector or camera 210 and light source 220 are shown as separate components. In various embodiments, image detector or camera 210 can include light source 220.

Figure 3:
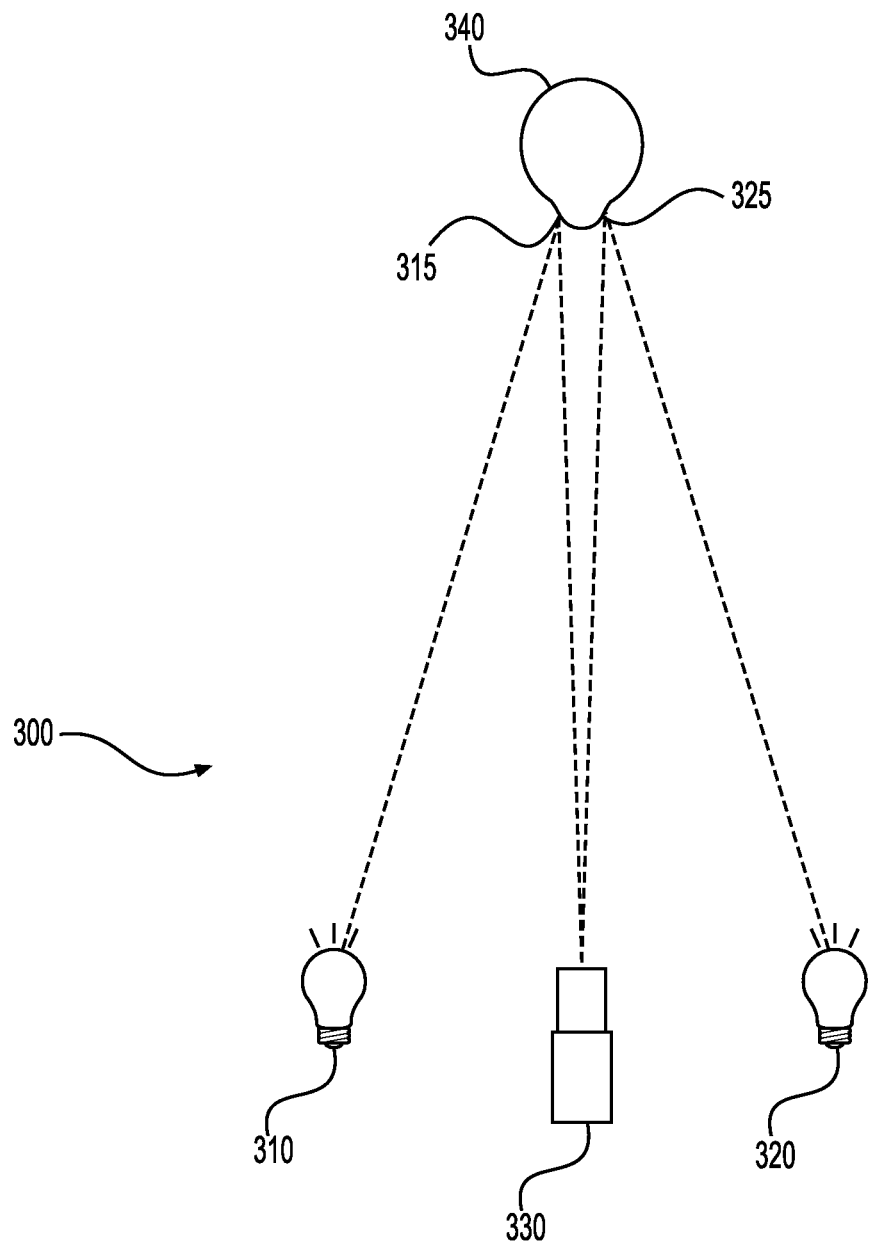
FIG. 3 illustrates an eye tracking camera configuration that uses widely separated illuminators to produce multiple corneal reflections from which the range from the camera to the eye can be estimated (prior art).

FIG. 3 illustrates an eye tracking camera configuration 300 that uses widely separated illuminators 310 and 320 to produce multiple corneal reflections 315 and 325 from which the range from the camera 330 to the eye 340 can be estimated.

Figure 4A:
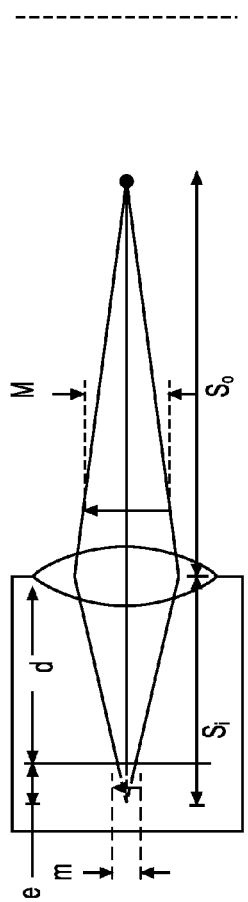
FIGS. 4A-4C, reproduced from U.S. Pat. No. 4,974,010 to Cleveland, illustrate the ray-trace optics of the inversion or non-inversion of the image of a point source of light based on the lens being focused before or beyond the point source (prior art).
Figure 4B:
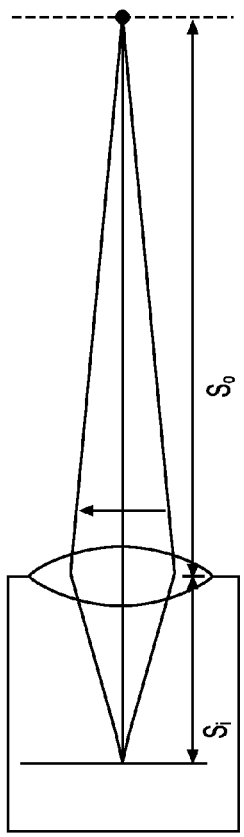
Figure 4C:
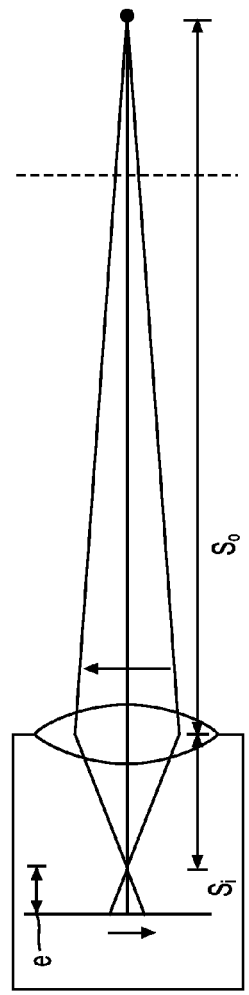

FIGS. 4A-4C, reproduced from U.S. Pat. No. 4,974,010 to Cleveland, illustrate the inversion or non-inversion of the image of a point source of light based on the lens being focused before or beyond the point source. From the inversion or non-inversion of the image the range from a camera to an eye can also be estimated.

Improved Asymmetric Aperture

As described above, many devices for focusing an imaging device on an eye are undesirable for many gaze or eye trackers, because they typically require additional equipment and/or measurement of the individual user's eye parameters to calibrate the range-measurement function, and may not provide the required range measurement accuracy. U.S. Pat. No. 4,974,010 to Cleveland provides an asymmetric aperture that can provide the range measurement accuracy required for eye tracking. A key drawback of the asymmetric aperture of FIG. 1A, however, is that it blocks a large percentage of the light reaching the camera's sensing means. Another key drawback is that the single illuminator is power limited in its ability to support eye tracking at longer ranges.

In various embodiments, the light gathering properties of an asymmetric aperture such as illustrated in FIG. 1A are improved by increasing both the light gathering opening of the aperture and the number of light producing light sources placed on the aperture. One important objective of various embodiments is to provide an asymmetric aperture design that utilizes a significantly larger portion of the camera lens. A second key objective of various embodiments is to optimize the tradeoff between the competing objectives of maximizing camera depth of field and maximizing the production of useful focus-condition information within the camera image.

A third important objective of various embodiments is to provide more illumination without significantly increasing the lateral size of the illuminator pattern. While it is well known in the eye tracking or eye tracking art to increase the amount of light by using multiple illuminators, the embodiments discussed here optimize the relative placement of the illuminators with respect to the eye tracker camera lens so as to maintain maximum resolution in the system's ability to resolve small differences in the lens focus condition.

Since a camera's image quality generally depends on a sufficient amount of light reaching the sensor, any aperture blockage that results from constructing asymmetries in the aperture shape (with respect to a conventional circular aperture) results in a requirement for increased illumination of the eye (with respect to the amount of light required for a circular aperture). Thus the asymmetric aperture of FIG. 1A, with its large blockage of the camera lens area, significantly increases the eye tracker's illumination requirement to obtain a high quality eye image. Also, it should be recalled, eye tracker illumination requirements increase with the range to the eye, so to increase the operational range of an eye tracker, it is generally necessary to increase its illumination power.

Multiple Illuminator Devices

One method for increasing the amount of light reaching a camera's sensor is to simply increase the power of the illuminator source. To generate a high quality camera image, however, it is required that the illuminator provide a uniform illumination over the area being photographed, and many illuminators, including LEDs, that are designed to provide uniform illumination are often limited in the maximum power they can produce from a single device. Thus, once the total illumination requirement for a camera exceeds the maximum power of a single illuminator device, it becomes necessary to use multiple illuminator devices. In eye tracking cameras it is generally desired to keep the size of the illuminator pattern as small as possible, thereby keeping the size of the corneal reflection at the eye as close to a virtual point source as possible. Thus, when increasing the number of illuminator devices above one, it is desired to keep the devices as close together as possible. Given a camera with the asymmetric aperture pattern of FIG. 1A, it is possible to a) use multiple illuminator devices, b) keep the cluster of illuminator devices small, and c) not increase the opaque blockage of the asymmetric aperture pattern—by placing up to three additional illuminator devices in the opaque regions (later defined as "tabs") between the individual transparent regions 101.

Figure 6:
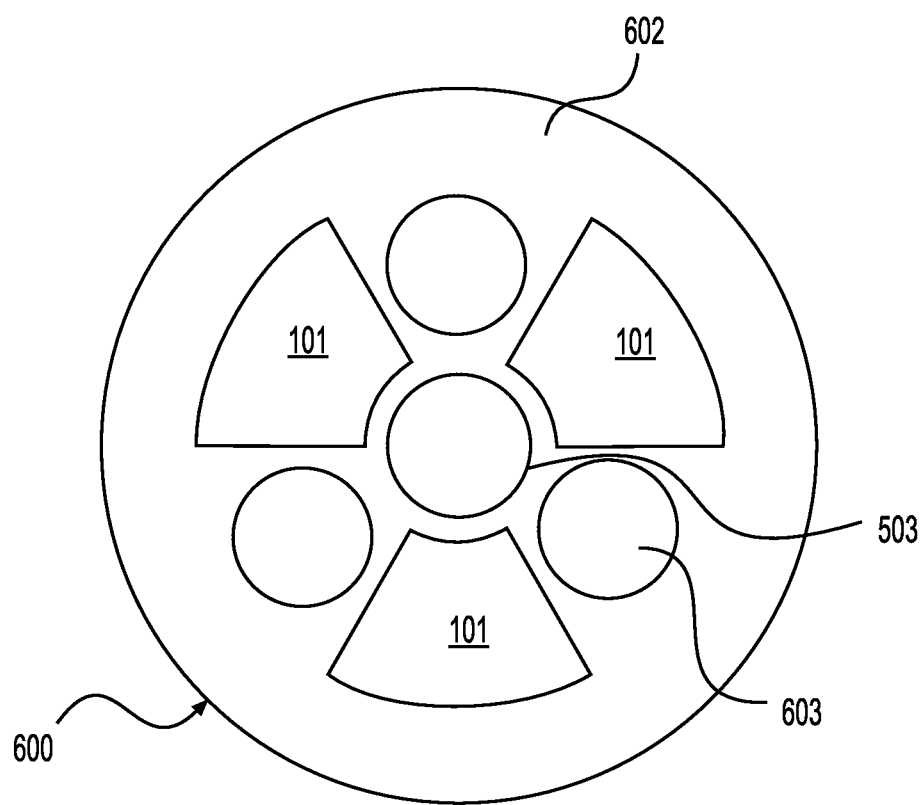
FIG. 6 illustrates a closed-center asymmetric aperture with three transparent openings and four illuminator devices, one illuminator mounted at the center of the lens and three mounted between the three transparent openings, in accordance with various embodiments.

FIG. 6 illustrates a closed-center asymmetric aperture with three transparent openings and four illuminator devices, in accordance with various embodiments. As shown in FIG. 6, a closed-center asymmetric aperture device for a camera has a) three transparent regions arranged in a circular pattern around the optic axis of the camera and b) a set of four illumination devices, up to one located at the center of the circle and three located around the circle between the three transparent regions.

Open Aperture Center

Figure 5:
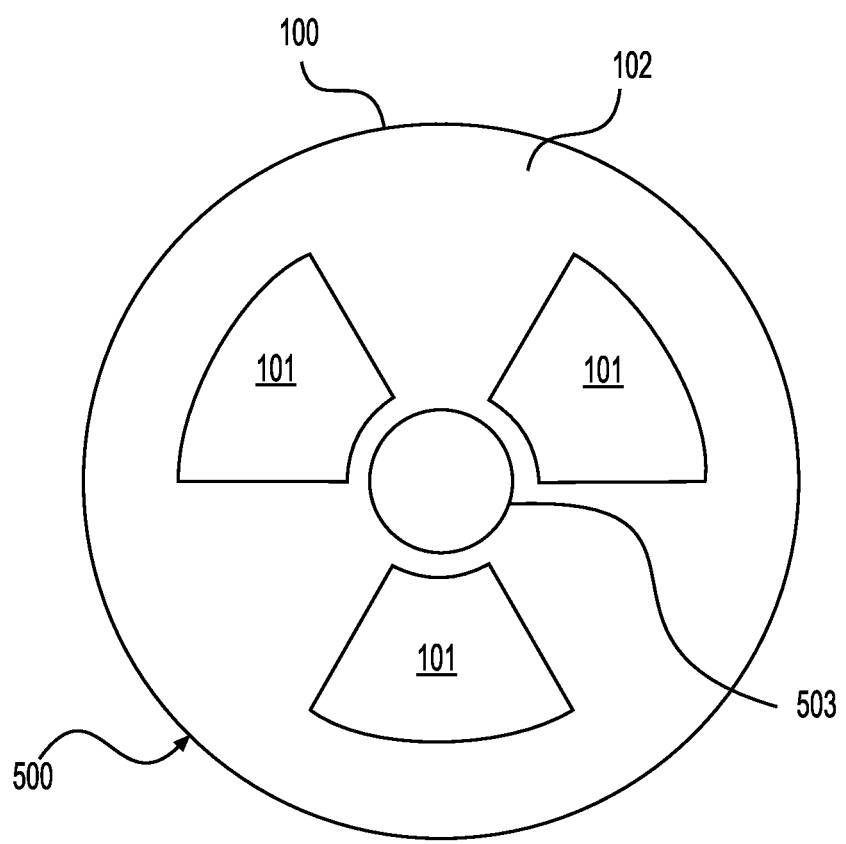
FIG. 5 illustrates a closed-center asymmetric aperture with three transparent openings and one illuminator device mounted at the center of the lens (prior art).

Note that the asymmetric aperture shape of FIG. 1A is opaque at the center. FIG. 5 illustrates a closed-center asymmetric aperture with three transparent openings and one illuminator device mounted at the center of the lens. As illustrated in FIG. 5, one reason to block the lens center is that it may be desired to place the eye tracker's illuminator 503 at the center of the lens, so as to produce camera co-axial illumination of the eye, which in turn produces the bright pupil effect.

Figure 7:
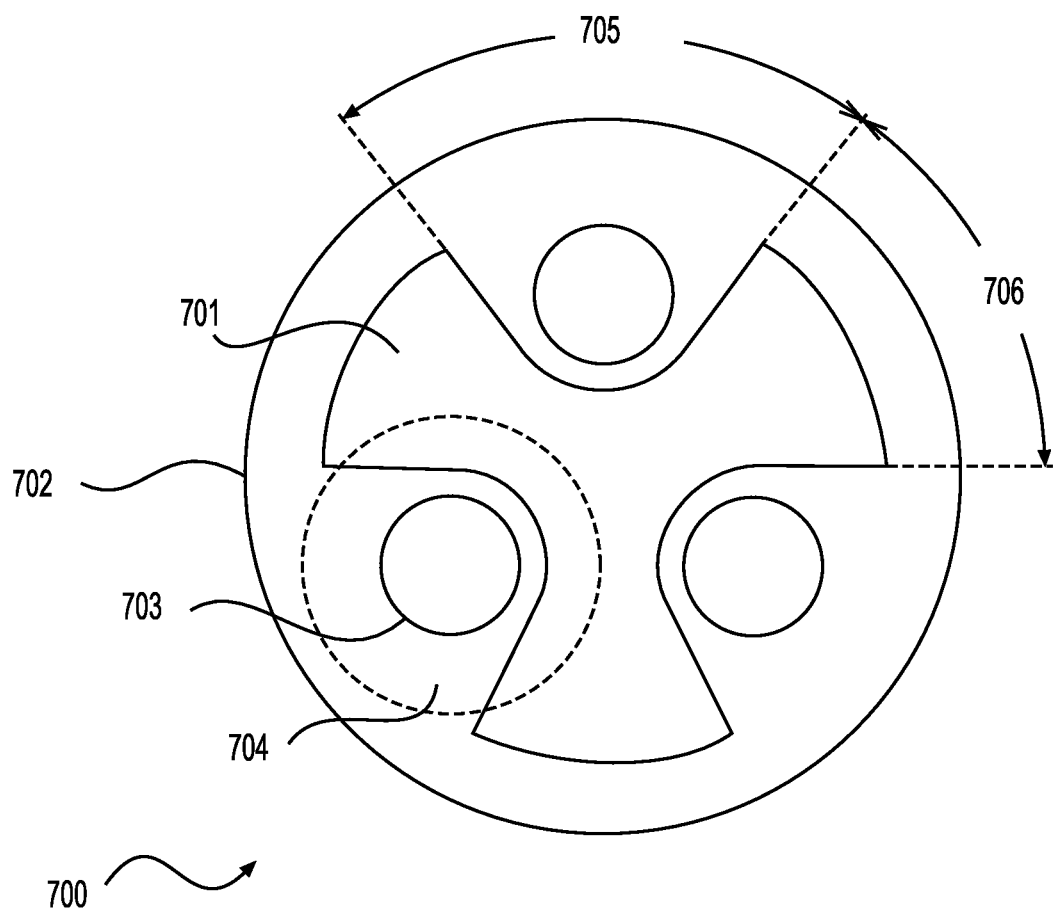
FIG. 7 is a front view of an open-center asymmetric aperture that optimizes both the opening of the aperture and the number of light sources, in accordance with various embodiments.

Another method for improving the light-collection properties of the asymmetric aperture of FIG. 1A is to remove the opaque region at the center of the aperture. FIG. 7 is a front view of an asymmetric aperture 700 with a transparent opening 701 that optimizes both the area of the aperture opening and the number of light sources, in accordance with various embodiments. In this open-center implementation, the asymmetric aperture 700 device consists of a) a single transparent opening, where the outer perimeter of the opening 701 is inscribed in an outer circle, and b) a set of three opaque areas, or "tabs" 704, that intrude into the outer circular perimeter. In preferred embodiments, the opaque intrusion tabs 704 are evenly, or approximately evenly, spaced around the perimeter of the opening, and the angular widths 705 of the tabs 704 are equal or approximately equal to the angular widths 706 of the aperture opening segments along the outer perimeter of the circle. This open-center triangular aperture pattern 700 retains the key feature that the inverted and non-inverted images are highly distinguishable, particularly if the angular widths 705 of the opaque intrusion tabs match the angular widths 706 of the transparent opening segments. At the same time, the open center of the lens allows the camera sensor to collect considerably more light than closed-center aperture of FIG. 1A.

Multiple Illuminators with an Open-Center Aperture

The open-center design of aperture 700, of course, precludes the placement of a single, coaxial illumination source at the center of the camera lens. However, in various embodiments a set of three illuminators 703 may be positioned very close to the lens center by installing them within the opaque intrusion tabs 704 as shown in FIG. 7. W. The three light sources 703 are light emitting diodes (LEDs), for example.

The asymmetric aperture opening 701 produces a pattern that resembles a hub with three spokes. The hub and threes spokes can also be described as a central lobe with three adjacent lobes. The three spokes or adjacent lobes of the opening provide the asymmetry with respect to typical spherical apertures. Although FIG. 7 shows only three spokes, one of ordinary skill in the art can appreciate that an asymmetric aperture can include any odd number of spokes or adjacent lobes, since an odd number of spoke lobes provides a distinguishable image shape when either inverted or uninverted, as occur when the lens is focused closer or farther than a point source image such as a reflection of an illuminator off an eye's corneal surface. The inverted or uninverted image of a point source, based on the camera's being focused too far or too near, is illustrated in FIGS. 4A-4C (reproduced from FIG. 3 of U.S. Pat. No. 4,974,010 to Cleveland). Specifically, FIGS. 4A-4C illustrate the ray-trace optics of the inversion or non-inversion of the image of a point source of light based on the lens being focused before or beyond the point source. Similarly, one of ordinary skill in the art can appreciate that an asymmetric aperture can include any odd number of light sources that can be placed in the opaque intrusion-tab regions 704 of the aperture.

By placing light sources 703 within the opaque intrusion-tab regions of the asymmetric aperture, the center of asymmetric aperture opening 701 can be left open, optimizing the amount of light that can pass through the aperture opening 701. By using more than one light illumination source, the amount of light that can reach the camera lens sensor is also increased.

Longitudinal Location of the Asymmetric Aperture

Figure 8:
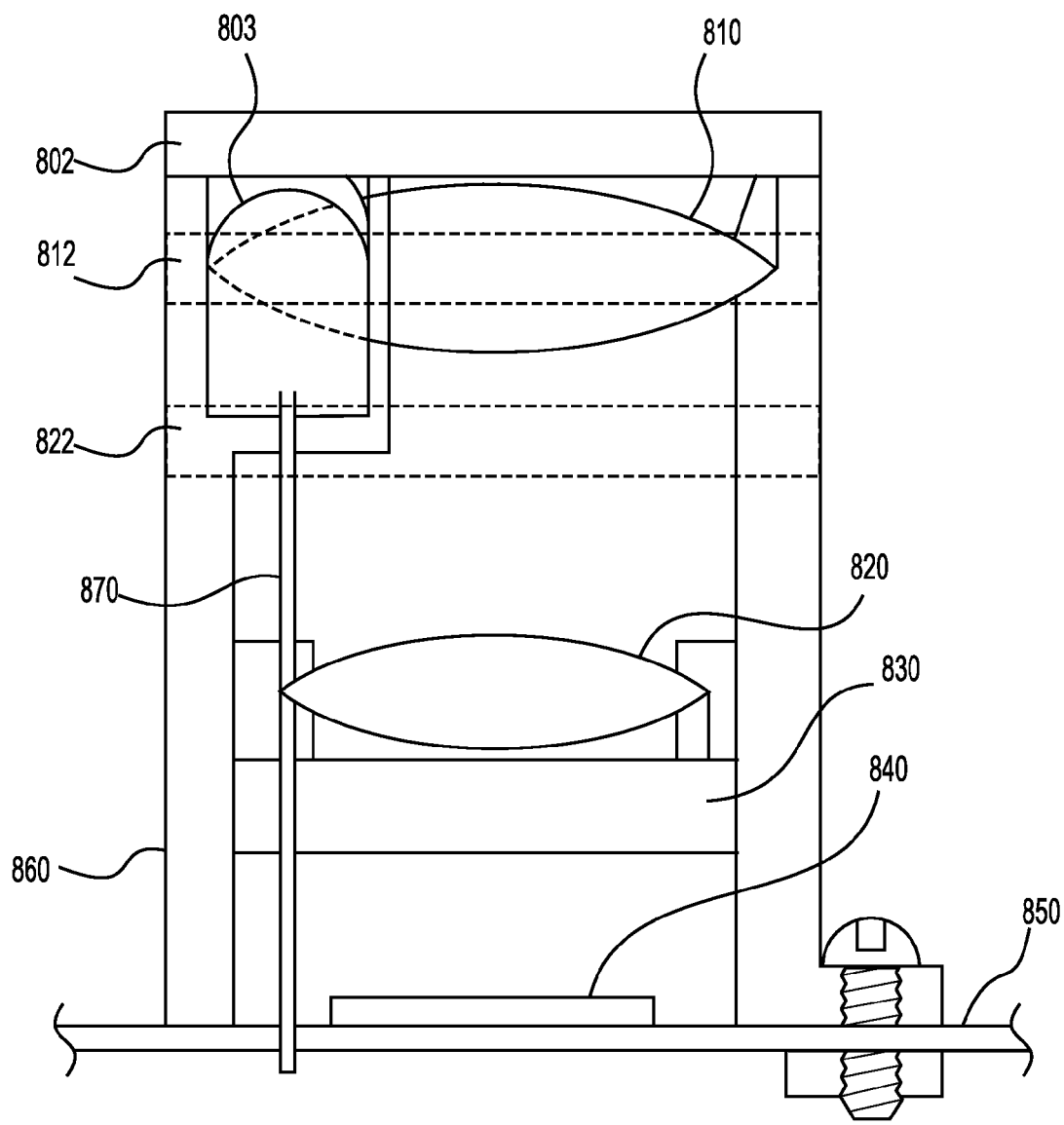
FIG. 8 is a cross-sectional side view of an image detector that includes the asymmetric aperture of FIG. 7, in accordance with various embodiments.

FIG. 8 is a cross-sectional side view of an image detector that includes the asymmetric aperture of FIG. 7, in accordance with various embodiments. Specifically, image detector assembly 800 includes a) an asymmetric aperture device 802, with an asymmetric aperture opening such as 701 shown in FIG. 7. Image detector assembly 800 further includes b) an objective lens element 810 (also referred to as objective lens), c) an exit lens element 820, and d) an optical filter 830 that may be used to minimize image noise from ambient light sources. Image detector assembly 800 further includes e) an image sensor 840, f) a printed circuit board 850 that mechanically and electronically supports the camera sensor 840, and g) illuminators 803. Image detector assembly 800 further includes h) electrical leads 870 that supply power from the circuit board 850 to the illuminators 803, and i) a lens-barrel frame 860 that mechanically houses the lens elements 810, 820, optical filter 830, printed circuit board 850 of the camera, illuminators 803, and asymmetric aperture device 802. Asymmetric aperture device 802 provides the asymmetric and, therefore, orientation distinguishable image received by image sensor 840.

In FIG. 8, asymmetric aperture device 802 is shown in front of objective lens element 810. Asymmetric aperture device 802, however, can be placed in an infinite number of locations along the longitudinal axis of lens-barrel frame 860. For example, asymmetric aperture device 802 may be placed a) out in front of objective lens element 810, as indicated by the location shown as 802 in FIG. 8, b) within objective lens element 810, as indicated by location 812, or c) behind objective lens element 810, as indicated by location 822.

In current implementations of cameras with asymmetric apertures, asymmetric aperture device 802 is located out in front of objective lens element 810, at the location shown as 802 in FIG. 8. This location out in front of objective lens element 810, however, presents two limitations. First, placing the aperture outside the lens extends the overall length of the camera apparatus, particularly if the illuminators are also mounted on the aperture device outside the objective lens. Second, from the optical standpoint of the point light source projecting the shape of the aperture onto the camera sensor, the optimum longitudinal location for the aperture opening resides at the plane where the lens's focus refraction occurs, i.e., at the longitudinal plane where the light rays bend the most. (See the location of the light-ray refraction in FIG. 4.) As long as the light source lies on the camera's central longitudinal axis, there is no distortion of the projected aperture shape—as long as the aperture device is centered on and located along the camera axis. As the point source moves off axis, however, the projected aperture shape as seen on the camera sensor distorts in proportion to two factors: a) the off-axis angle of the point source within the camera field of view, and b) the longitudinal distance between the aperture plane and the lens's primary refraction plane. Thus, to accurately measure the focus condition for point-source objects throughout the camera's angular field of view, the optimum location for the aperture-device plane is the longitudinal center of the objective lens.

Figure 10:
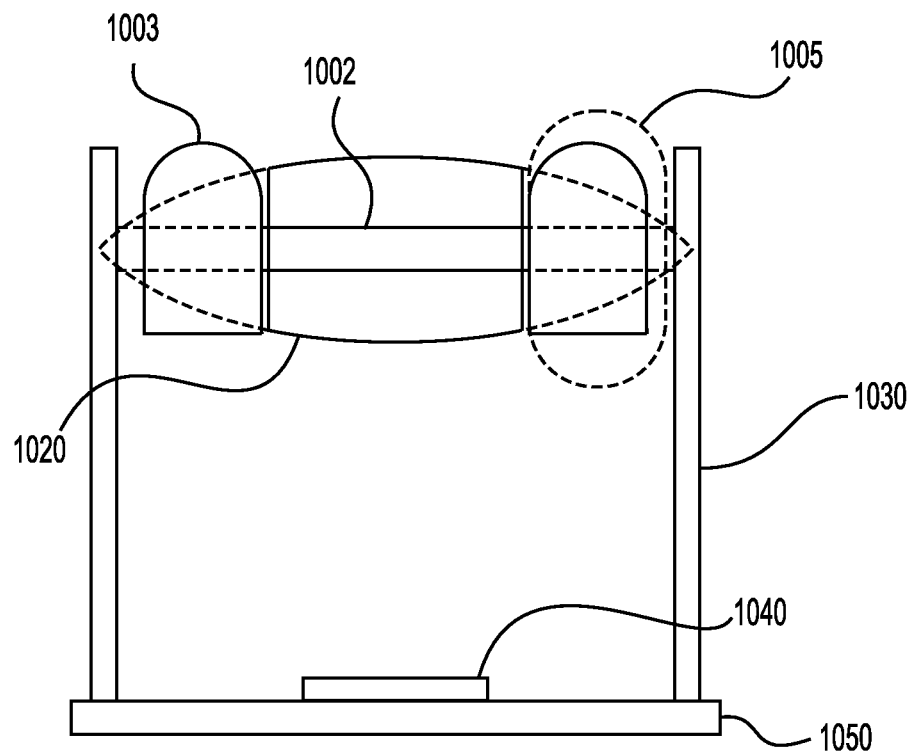
FIG. 10 is a schematic diagram of a lens/aperture/illuminator assembly in which the aperture device and the illuminators are positioned in the same plane as objective lens, in accordance with various embodiments.

FIG. 10 is a schematic diagram of a lens/aperture/illuminator assembly 1010 in which asymmetric aperture device 1002 and illuminators 1003 are positioned in the same plane as objective lens element 1020, in accordance with various embodiments.

Figure 9:
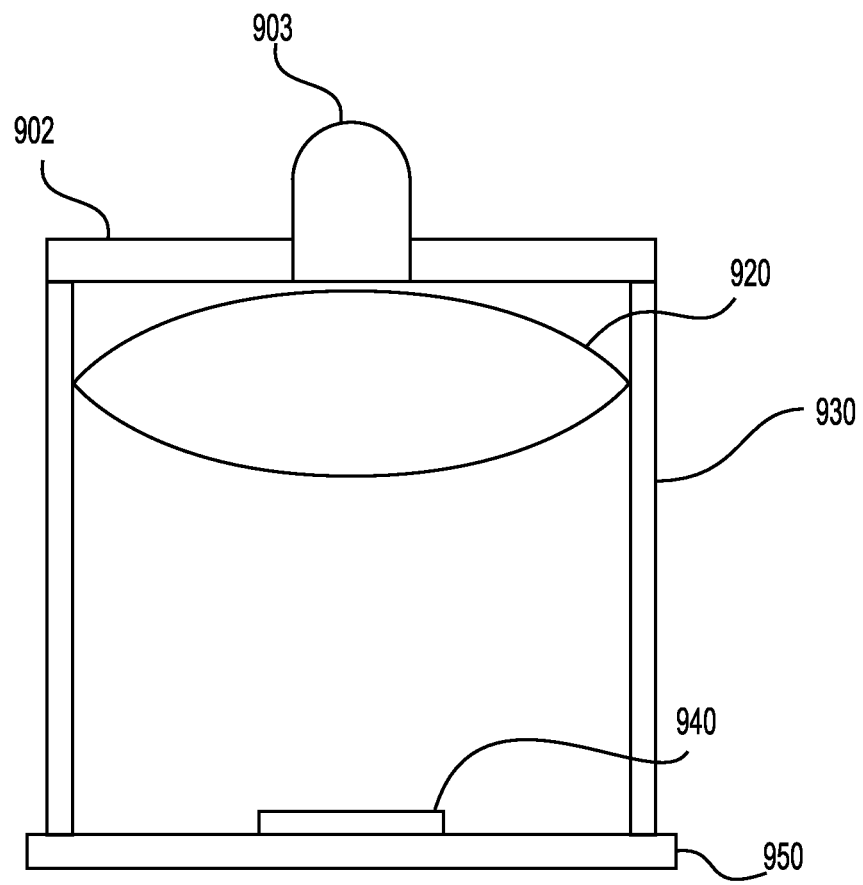
FIG. 9 is a schematic diagram of a lens/aperture/illuminator assembly in which the aperture device and the illuminators are positioned in front of the objective lens (prior art).

In one embodiment of this invention, the plane of the asymmetric aperture device is embedded within the objective lens of the camera, i.e., the opaque material forming the lens aperture is embedded within the body of the camera's objective lens. As shown in FIG. 10, asymmetric aperture device 1002 is embedded in an objective lens 1020. In comparison, FIG. 9 is a schematic diagram of a prior art lens/aperture/illuminator assembly 900 in which aperture device 902 and illuminators 903 are positioned in front of objective lens element 920. As shown in FIG. 9, prior art assembly 900 also includes optical filter 930, image sensor 940, and printed circuit board 950.

Minimizing the Length of Lens/Aperture/Illuminator Assembly

In addition to showing asymmetric aperture device 1002 being embedded in the camera's objective lens element 1020, FIG. 10 also illustrates illuminators 1003 mounted at a longitudinal position such that the front of illuminators 1003 do not extend forward of the front of objective lens element 1020, in accordance with various embodiments. This illuminator configuration, with the illuminators a) being close to one another in the camera lateral plane and b) existing behind the front of objective lens element 1020 along the longitudinal axis, is useful for cases where it is desired to minimize the overall size of the camera equipment.

As can be seen in FIG. 10, however, illuminators 1003 exist within the physical volume of a conventionally designed objective lens. To position illuminators 1003 in these optimal locations, it is necessary to remove material from the objective lens to create space for the illuminators. In this discussion, the spaces cut out from what would otherwise be a conventional objective lens are called "lens cutouts." The lens cutouts 1005 are shown in FIG. 10 by dotted line. Though incorporating these lens cutouts in the objective lens may add to the lens production cost, the camera performance increases in measuring focus condition often justify the expense.

In accordance with the discussion above, one embodiment of this invention is a camera employing a) illuminators, b) an objective lens, and c) an asymmetric aperture device with opaque intrusion areas, wherein lens cutouts are incorporated into the camera's objective lens at lateral locations corresponding to the illuminator locations. The lens cutouts permit the physical location of the illuminators within the lens cutout volumes behind the front surface of the lens.

In some cases, it may not be practical or economically feasible to embed the asymmetric aperture device within the camera's objective lens. In these cases, and where it is also desired to minimize the overall length of the camera equipment, the asymmetric aperture device may be positioned behind the objective lens, as illustrated in FIG. 11, in accordance with various embodiments.

Figure 11:
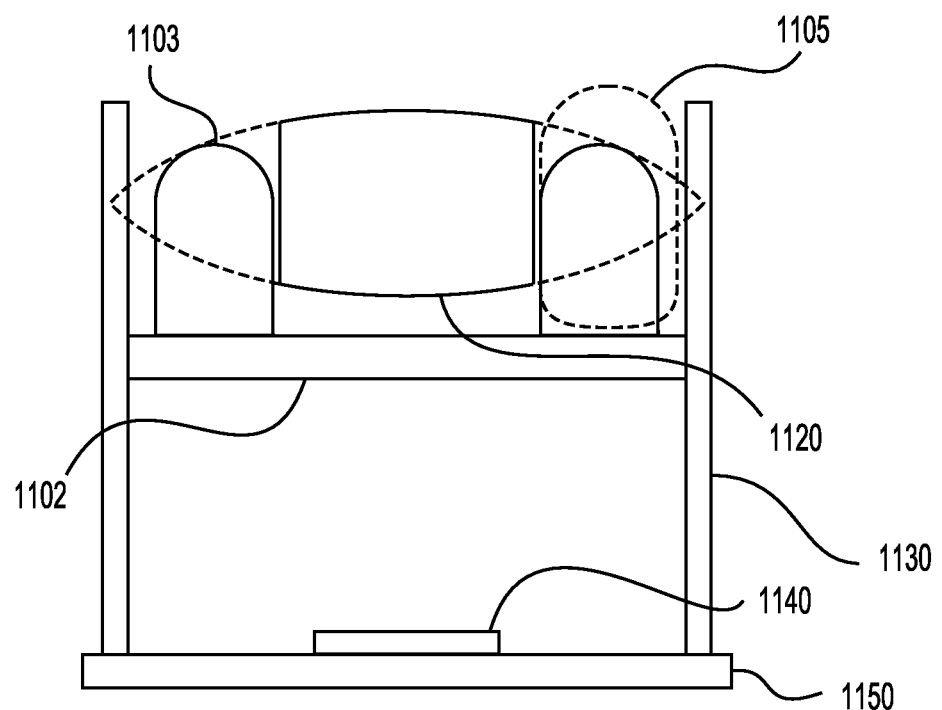
FIG. 11 is a schematic diagram of a lens/aperture/illuminator assembly in which the aperture device is positioned behind the objective lens, in accordance with various embodiments.

FIG. 11 is a schematic diagram of a lens/aperture/illuminator assembly 1100 in which aperture device 1102 is positioned behind objective lens element 1120, in accordance with various embodiments. As shown in FIG. 11, lens/aperture/illuminator assembly 1100 also includes optical filter 1130, image sensor 1140, printed circuit board 1150, and lens cutouts 1105 (illustrated by dotted line).

Though locating the asymmetric aperture device behind the objective lens may avoid the cost of embedding the aperture device in the objective lens, it is still necessary to include the lens cutouts in the objective lens if the illuminators 1103 are not to be placed out in front of the lens.

In various embodiments, an open-center asymmetric aperture device includes a single transparent opening and a set of opaque intrusion areas. An outer perimeter of the single transparent opening is inscribed in a circle and the set of opaque intrusion areas intrude into the outer perimeter of the inscribed circle.

In various embodiments, the set of opaque intrusion areas comprise a set of three opaque intrusion areas. For example, the three opaque intrusion areas are evenly or approximately evenly spaced around the outer perimeter of the single transparent opening. For example, the angular widths of the three opaque intrusion areas are equal or approximately equal to the angular widths of the aperture-opening segments along the outer perimeter of the inscribed circle.

In various embodiments, the open-center asymmetric aperture device further includes multiple light illumination sources located within the set of opaque intrusion areas.

In various embodiments, a method for fabricating an open-center asymmetric aperture device is provided. A single transparent opening is inscribed in a circle. A set of opaque intrusion areas are made to intrude into the outer perimeter of the inscribed circle.

In various embodiments, a closed-center asymmetric aperture device for a camera includes a plurality of transparent regions arranged in a circular pattern around an optical axis of a camera and a set of illumination devices. One illumination device is located at the center of the circular pattern, and two or more additional illumination devices are located around the circular pattern between the plurality of transparent regions.

In various embodiments, the plurality of transparent regions comprise three transparent regions.

In various embodiments, the set of illumination devices comprises a set of up to four illumination devices, and the two or more additional illumination devices comprise three illumination devices.

In various embodiments, a method for fabricating a closed-center asymmetric aperture device for a camera. A plurality of transparent regions arranged in a circular pattern are created around an optical axis of a camera. One illumination device is placed at the center of the circular pattern, and two or more additional illumination devices are placed around the circular pattern between the plurality of transparent regions.

A camera employing an asymmetric aperture device includes an objective lens and an asymmetric opaque aperture device. The asymmetric opaque aperture device includes a single transparent opening and a set of opaque intrusion areas. An outer perimeter of the single transparent opening is inscribed in a circle. The set of opaque intrusion areas intrude into the outer perimeter of the inscribed circle.

In various embodiments, the asymmetric opaque aperture device is embedded within the objective lens of the camera.

In various embodiments, the asymmetric opaque aperture device is located out in front of the objective lens of the camera.

In various embodiments, the asymmetric opaque aperture device is located behind the objective lens of the camera.

In various embodiments, the asymmetric opaque aperture device includes multiple light illumination sources.

In various embodiments, a method for fabricating a camera employing an asymmetric aperture device is provided. The camera is made to include an objective lens and an asymmetric opaque aperture device. The asymmetric opaque aperture device is made to include a single transparent opening and a set of opaque intrusion areas. An outer perimeter of the single transparent opening is inscribed in a circle. The set of opaque intrusion areas are made to intrude into the outer perimeter of the inscribed circle.

In various embodiments, a camera includes a plurality of illuminators, an objective lens, and an asymmetric aperture device with opaque intrusion areas. Material is removed from the objective lens to create spaces for the plurality of illuminators. The spaces are lens cutouts. The lens cutouts are incorporated into the objective lens of the camera at lateral locations corresponding to locations of the plurality of illuminators, the lens cutouts permitting the plurality of illuminators to be located within a physical volume of the objective lens.

In various embodiments, the asymmetric aperture device is embedded within the objective lens of the camera.

In various embodiments, the asymmetric aperture device is located out in front of objective lens of the camera.

In various embodiments, the asymmetric aperture device is located behind the objective lens of the camera.

In various embodiments, the asymmetric aperture device comprises multiple light illumination sources.

In various embodiments, a method for fabricating a camera is provided. The camera is made to include a plurality of illuminators, an objective lens, an objective lens, and an asymmetric aperture device with opaque intrusion areas. Material is removed from the objective lens to create spaces for the plurality of illuminators. The spaces are lens cutouts. The lens cutouts are incorporated into the objective lens of the camera at lateral locations corresponding to locations of the plurality of illuminators, the lens cutouts permitting the plurality of illuminators to be located within a physical volume of the objective lens.

Free Head Motion

An important objective of many eye trackers is to allow the user to move his head freely while the eye tracker continues to track the user's gaze with high accuracy. Typical head motions involve moving (translating) the head side to side, up and down, and back and forth; and involve rotating the head forward and back (pitching or nodding), rotating the face left to right (yawing or shaking), and rotating the head toward one shoulder or the other (rolling). One method for minimizing head motion with respect to an eye tracking device is to place the eye tracker device on the user's head, attached to a pair of glasses for example. In many applications, however, it is desired to position the eye eye tracking device at a remote, off-head location. Accommodating head motion with respect to the eye tracker platform is particularly relevant to the objective of capturing high quality, high resolution eye images in remote eye trackers.

Figure 12:
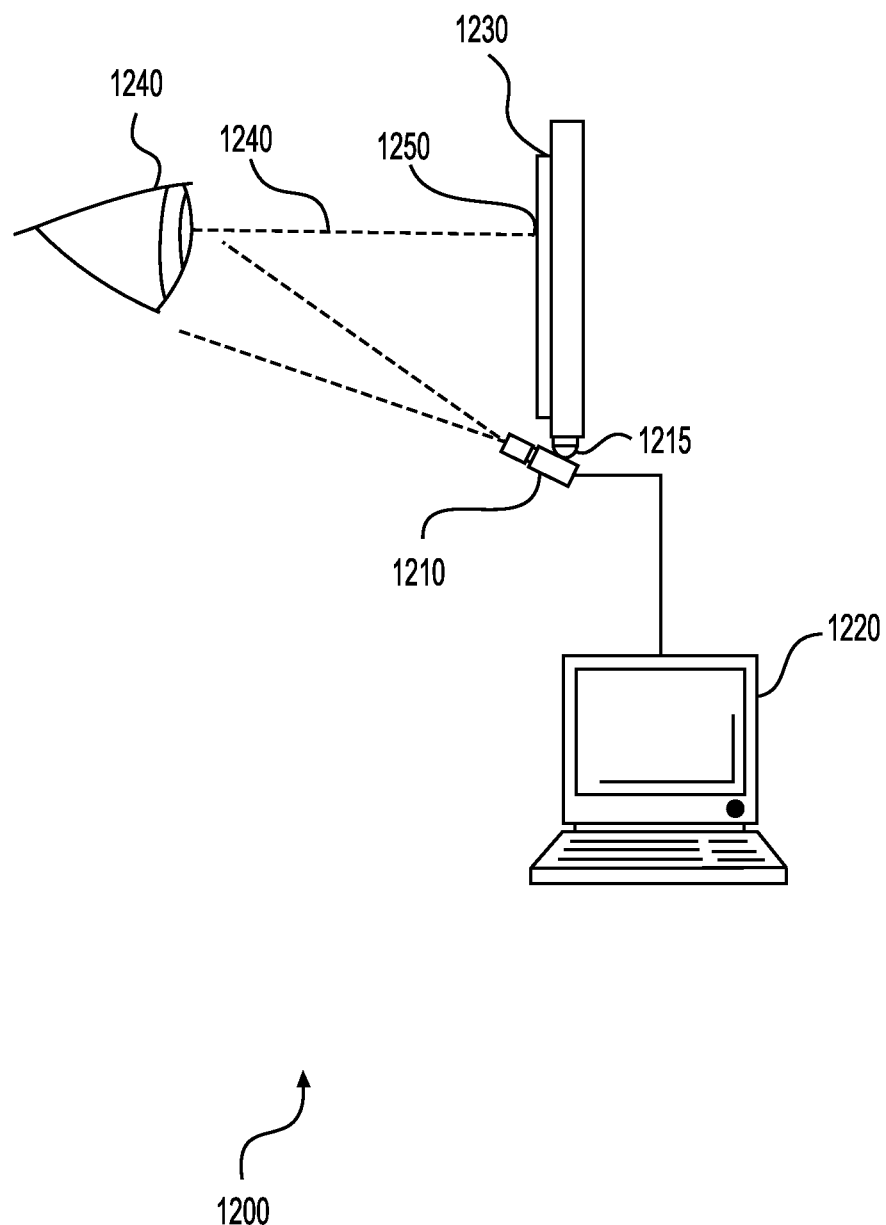
FIG. 12 is a schematic diagram showing an eye tracker that includes a mechanized gimbal, in accordance with various embodiments.

To accommodate variable positions and orientations of the head with respect to the eye tracker platform, non-head mounted, i.e. remote, eye trackers may include mechanized gimbal devices to keep the eye tracker camera(s) physically pointed at, focused on, and/or zoomed on the user's eye(s). As illustrated in FIG. 12, a motorized pan-tilt device, such as a gimbal 1215, may be used, for example, to keep the camera's view direction pointed at the eye or eyes; a focus motor (not shown in FIG. 12) may be used to keep the eye(s) in focus; or a zoom motor (not shown in FIG. 12) may be used to keep a desired zoom condition on the eye(s). Eye trackers that utilize such mechanical means to automatically point, focus and/or zoom their eye tracking cameras on the eyes are sometimes referred to as eyefollowers.

Gimbal-Based Eye Tracker (Eyefollower)

As described above, the motorized gimbal mechanisms of conventional eyefollowers are too large, heavy, and expensive to be built into handheld devices where it would be desirable to incorporate eye tracking devices.

In various embodiments, the size, weight, and power consumption of gimbal based eye tracking devices is reduced by using microelectromechanical systems, commonly referred to as MEMS, to control the physical camera positioning and focusing functions. The incorporation of MEMS into eyefollower architectures represents a critical advance in eye tracking technology because it enables the ultimate miniaturization of eyefollower devices.

FIG. 12 is a schematic diagram showing an eye tracker 1200 that includes an eyefollower, in accordance with various embodiments. Eye tracker 1200 includes camera 1210 (including camera body and camera lens), gimbal 1215, and processor 1220. The eyefollower portion of eye tracker 1200 includes, for example, a mechanical configuration comprising gimbal 1215, and a motorized lens (not shown) for camera 1210 that implements a variable-focus range. The eyefollower portion of eye tracker 1200 may also include a motorized zoom capability (not shown) for camera 1210 that implements a variable zoom. Note that camera 1210 can also include an illumination source (not shown).

In FIG. 12, the gimbal 1215 of eye tracker 1200 controls the yaw (pan) and pitch (tilt) of camera 1210, which, in turn, are used to follow a user's eye 1240 as the user moves his head and/or eye 1240 from side-to-side and up and down, respectively. The motorized lens for camera 1210 is used to follow the user's eye 1240 as the user moves his head forward or backward, and it may also be used in the computation of the range from the camera to the eye based on a measurement of the lens length required to put the eye in focus. (U.S. Pat. No. 4,974,010 to Cleveland et al. discloses a focus analysis system comprising a) a point source whose focus condition is to be measured, b) a camera including a lens, an asymmetric aperture with a noncircular shape of distinguishable orientation and a sensor for capturing the image formed by the lens the aperture, and c) an image processor that analyzes the captured image and determines the focus condition of the point light source based on the point source's image as shaped by the asymmetric aperture. This focus analysis system is particularly useful in video eye trackers because the reflection of the eye tracker's illuminator off the corneal surface of the user's eye, commonly called the corneal reflection, is a virtual point light source that is precisely tied to the location of the eye in space.) The motorized zoom for camera 1210 may be used to control the desired size, i.e., pixel resolution, of the eye image within the camera image as the user moves his head forward and backward. Gimbal 1215 can be optionally secured to display 1230, mechanically linking the coordinate system of camera 1210 to display 1230, for example.

Though gimbal 1215 in FIG. 12 can be used to rotate the entire camera to continually point at the user's eye(s), it is also possible to rotate a mirror placed in front of the camera lens so as to steer the camera's view direction toward the eye, thus requiring the rotation of only a small, light mirror rather than a generally larger and heavier camera and lens assembly. U.S. Pat. No. 5,090,797 to Cleveland et al. discloses a mirror control system that can be used in an eye tracker comprising a) a camera and with a lens, b) a pan/tilt mirror with motors to drive the pan and tilt angles, c) an image processor that processes the camera's image of a user's eye and computes the location of the eye within the camera image frame, d) a mirror command calculator that calculates pan/tilt commands required to keep the eyes within the camera image, and e) motor controllers that convert the pan/tilt commands to motor control signals that actuate the motors. Currently, gimbal implementations involving either mirror rotation or full camera/lens rotation are too large and bulky for implementation in many applications. The size and weight of these eye tracker gimbal configurations are significantly miniaturized by the use of MEMS, thus enabling many applications that are not now practical.

The processor 1220 of eye tracker 1200 shown in FIG. 12 typically performs several of the eye tracker functions required to measure an eye's gazepoint. First, it receives the image of the eye from the eye tracker camera. It then processes the eye image to detect the eye within the image and determine the location of the eye within the image. If the eye tracker has eyefollower capabilities, the processor also executes control loop algorithms required to keep the camera pointed at, focused on, and zoomed on eye 1240 as the user moves his head. Processor 1220 also executes, for example, algorithms used to solve rigorous trigonometric gazepoint tracking equations, referred to as "explicit raytrace algorithms." These explicit raytrace algorithms are used to accurately predict the user's gazepoint 1250 on display 1230, fully accommodating the variable camera geometry and the moving head and/or eye 1240. U.S. Pat. No. 7,686,451 to Cleveland discloses such explicit raytrace algorithms.

As discussed above, a key performance objective of most video eye trackers is to measure the coordinates of where a person is looking with a certain level of gazepoint tracking accuracy. To achieve a given degree of accuracy, it is necessary that the eye tracking camera produces a high quality video image stream of the eye with spatial, illumination and temporal resolutions sufficient to support the gazepoint calculation from the captured video images.

It is also an objective of many modern eye trackers to permit ever greater freedom of user head movement while the eye trackers continue to track the gaze with equivalent or increasing accuracy. One approach to increasing the volume of trackable head space is to increase a fixed camera's 3-dimensional volume of view. To maintain gazepoint tracking accuracy with a fixed camera, however, the increased field of view must be accompanied by a proportional increase in the number of pixels on the camera image sensor, so as to maintain a high resolution of the camera's eye image.

Another approach to increasing the volume of trackable head space is to allow the camera to physically rotate, refocus and move, much the same way live eyes do. A telephoto, narrow-field-of-view camera can produce a high resolution image of the eye with a comparatively small number of total sensor pixels, and freedom of user head movement is achieved by placing the camera on a controlled pan/tilt gimbal that keeps the camera(s) pointed at and focused on the user's eyes as the user moves his head around with respect to the eye tracker platform.

Current implementations of gimbal-based eye trackers typically utilize stepper motors and/or analog servo motors to rotate the camera body and focus the lens. The use of these types of actuators has several disadvantages. Various embodiments minimize the size, weight, power consumption, cost, and noise of gimbal based eye trackers by using microelectromechanical systems, commonly referred to as MEMS, to control the physical camera positioning and focusing functions.

Computer-Implemented System

Figure 13:
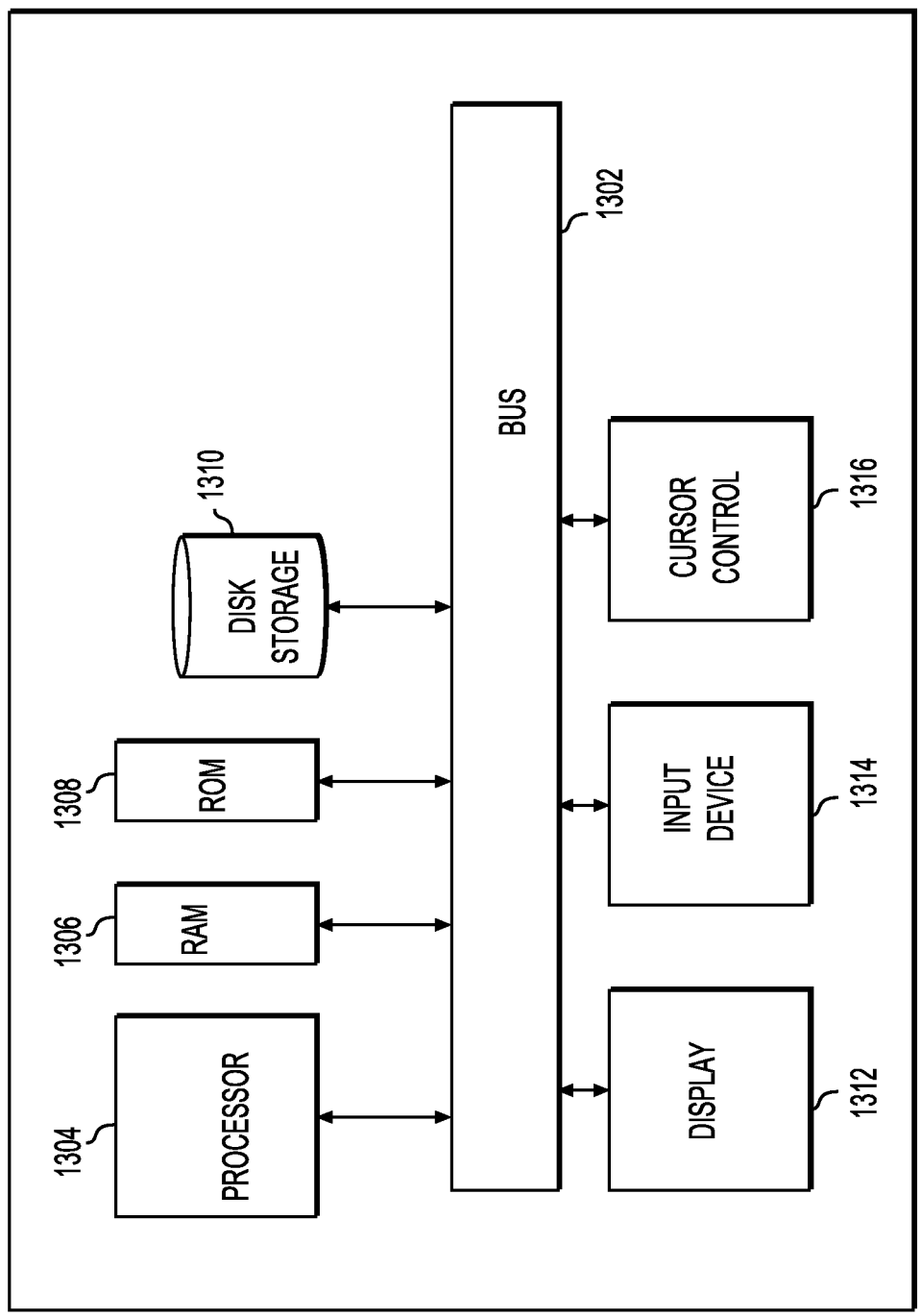
FIG. 13 is a block diagram that illustrates a computer system, in accordance with various embodiments.

While computer processors perform the automated image processing functions within non-mechanized eye trackers, they also execute the motor control functions in gimbal-based eye trackers. FIG. 13 is a block diagram that illustrates a computer system 1300, in accordance with various embodiments. Computer system 1300 includes a bus 1302 or other communication mechanism for communicating information, and a processor 1304 coupled with bus 1302 for processing information. Computer system 1300 also includes a memory 1306, which can be a random access memory (RAM) or other dynamic storage device, coupled to bus 1302 for determining base calls, and instructions to be executed by processor 1304. Memory 1306 also may be used for storing temporary variables or other intermediate information during execution of instructions to be executed by processor 1304. Computer system 1300 further includes a read only memory (ROM) 1308 or other static storage device coupled to bus 1302 for storing static information and instructions for processor 1304. A storage device 1310, such as a magnetic disk or optical disk, is provided and coupled to bus 1302 for storing information and instructions.

Computer system 1300 may be coupled via bus 1302 to a display 1312, such as a cathode ray tube (CRT), liquid crystal display (LCD), or 3-dimensional display, for displaying information to a computer user. An input device 1314, including alphanumeric and other keys, is coupled to bus 1302 for communicating information and command selections to processor 1304. Another type of user input device is cursor control 1316, such as a mouse, a trackball or cursor direction keys for communicating direction information and command selections to processor 1304 and for controlling cursor movement on display 1312. This input device typically has two degrees of freedom in two axes, a first axis (i.e., x) and a second axis (i.e., y), that allows the device to specify positions in a plane.

A computer system 1300 can perform the present teachings. Consistent with certain implementations of the present teachings, results are provided by computer system 1300 in response to processor 1304 executing one or more sequences of one or more instructions contained in memory 1306. Such instructions may be read into memory 1306 from another computer-readable medium, such as storage device 1310. Execution of the sequences of instructions contained in memory 306 causes processor 1304 to perform the process described herein. Alternatively hard-wired circuitry may be used in place of or in combination with software instructions to implement the present teachings. Thus implementations of the present teachings are not limited to any specific combination of hardware circuitry and software.

The term "computer-readable medium" as used herein refers to any media that participates in providing instructions to processor 1304 for execution. Such a medium may take many forms, including but not limited to, non-volatile media, volatile media, and transmission media. Non-volatile media includes, for example, optical or magnetic disks, such as storage device 1310. Volatile media includes dynamic memory, such as memory 1306. Transmission media includes coaxial cables, copper wire, and fiber optics, including the wires that comprise bus 1302.

Common forms of computer-readable media include, for example, a floppy disk, a flexible disk, hard disk, magnetic tape, or any other magnetic medium, a CD-ROM, any other optical medium, punch cards, papertape, any other physical medium with patterns of holes, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 1304 for execution. For example, the instructions may initially be carried on the magnetic disk of a remote computer. The remote computer can load the instructions into its dynamic memory and send the instructions over a telephone line using a modem. A modem local to computer system 1300 can receive the data on the telephone line and use an infra-red transmitter to convert the data to an infra-red signal. An infra-red detector coupled to bus 1302 can receive the data carried in the infra-red signal and place the data on bus 1302. Bus 1302 carries the data to memory 1306, from which processor 1304 retrieves and executes the instructions. The instructions received by memory 1306 may optionally be stored on storage device 1310 either before or after execution by processor 1304.

In accordance with various embodiments, instructions configured to be executed by a processor to perform a method are stored on a non-transitory and tangible computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Systems and Methods of Miniaturization

As described above, eye tracking systems have included large gimbal-based cameras or imaging devices for capturing images from one or more eyes. Recently, camera lenses and imaging devices have gotten smaller, due to technological advances in areas including, but not limited to, hand-held devices such as smartphones. As a result, a need has developed to miniaturize or reduce the overall size of eye tracking systems along with their camera lenses and imaging devices.

Some eye trackers, sometimes called eyefollowers, utilize additional mechanical devices such as gimbals and autofocusing mechanisms to point, focus and zoom the cameras on user's eyes. These point, focus and zoom actuator devices within the eyefollower, which in many cases are significantly larger than the camera itself, also need to be miniaturized.

In various embodiments, an eye tracker that includes an eyefollower is miniaturized or made smaller by using microelectromechanical systems (MEMSs), also referred to as MEMS devices. MEMSs can also be referred to as micro-electro-mechanical, microelectronic, or microelectromechanical systems, micromachines, or micro systems technology (MST). MEMSs can also include nanoelectromechanical systems (NEMS) and nanotechnology. By producing highly controllable, large amplitude electromagnetic forces from small volumes of material, MEMSs can be used, for example, to replace stepper motors, analog servo motors and complicated gear trains typically used in conventional eyefollowers. The use of MEMS significantly reduces the size, weight, power consumption, cost and noise of gimbal based eye trackers, ultimately making it feasible to implement head-free eye tracking in small, hand-held devices such as smart phones.

Pan/Tilt Control

To decrease the overall size of an eyefollower system, MEMSs are used in various embodiments to position an eye tracker camera's view direction. As discussed earlier, pointing an eye tracker's camera's view direction can be achieved either directly, by rotating the camera/lens assembly, or indirectly, by placing a pivoting mirror in front of the lens and rotating only the mirror.

In embodiments where the whole camera (i.e., including the camera body and the camera lens) is rotated, the camera may be mounted on a pan-tilt gimbal platform, and a small gimbal platform may be fabricated using MEMS devices.

Figure 14:
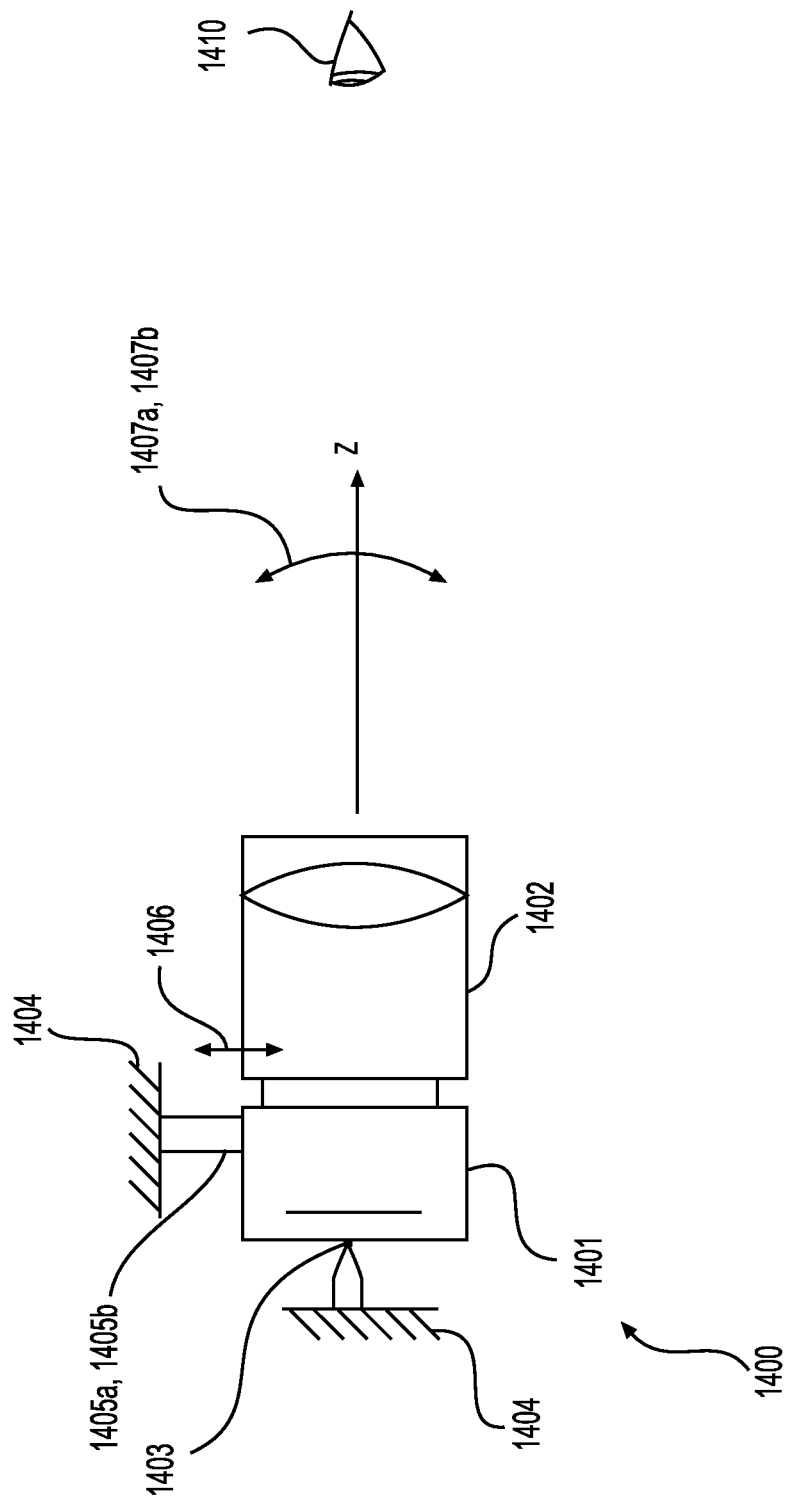
FIG. 14 illustrates an exemplary camera pan/tilt control mechanism with MEMS actuators used to control the viewing direction of the camera by controlling the pan and tilt angles of the camera's body/lens assembly with respect to the eyefollower's chassis, in accordance with various embodiments.

Given that MEMS actuators are small, however, yet even smaller eyefollower configurations can be implemented by attaching the MEMS actuators directly to the camera body, rather to a pan/tilt platform that in turn supports the camera. FIG. 14 illustrates one embodiment 1400 of an eyefollower pan/tilt control mechanism employing MEMS devices to control the pointing direction of the camera body and lens, in accordance with various embodiments. In this example, camera body 1401 is attached to camera lens 1402 and the camera body is attached to camera pivot point 1403 that is anchored to eyefollower chassis 1404. A linear MEMS actuator 1405a, 1405b, attached at one end to eyefollower chassis 1404, is attached at the other end to the side of camera body 1401 at a longitudinal position forward of the camera pivot point 1404. The actuator's linear direction of travel 1406 is perpendicular to the camera axis Z, resulting in an angular travel of the camera. There are two linear actuators: pan actuator 1405a attached to one side of the camera, whose motion results in the camera rotating in horizontal pan plane 1407a; and yaw actuator 1405b attached to the top or bottom of the camera, whose motion results in the camera rotating in vertical tilt plane 1407b. As eye 1410 moves side to side or up and down, actuators 1405a, 1405b rotate camera body 1401 and lens 1402 to follow eye 1410.

Figure 15:
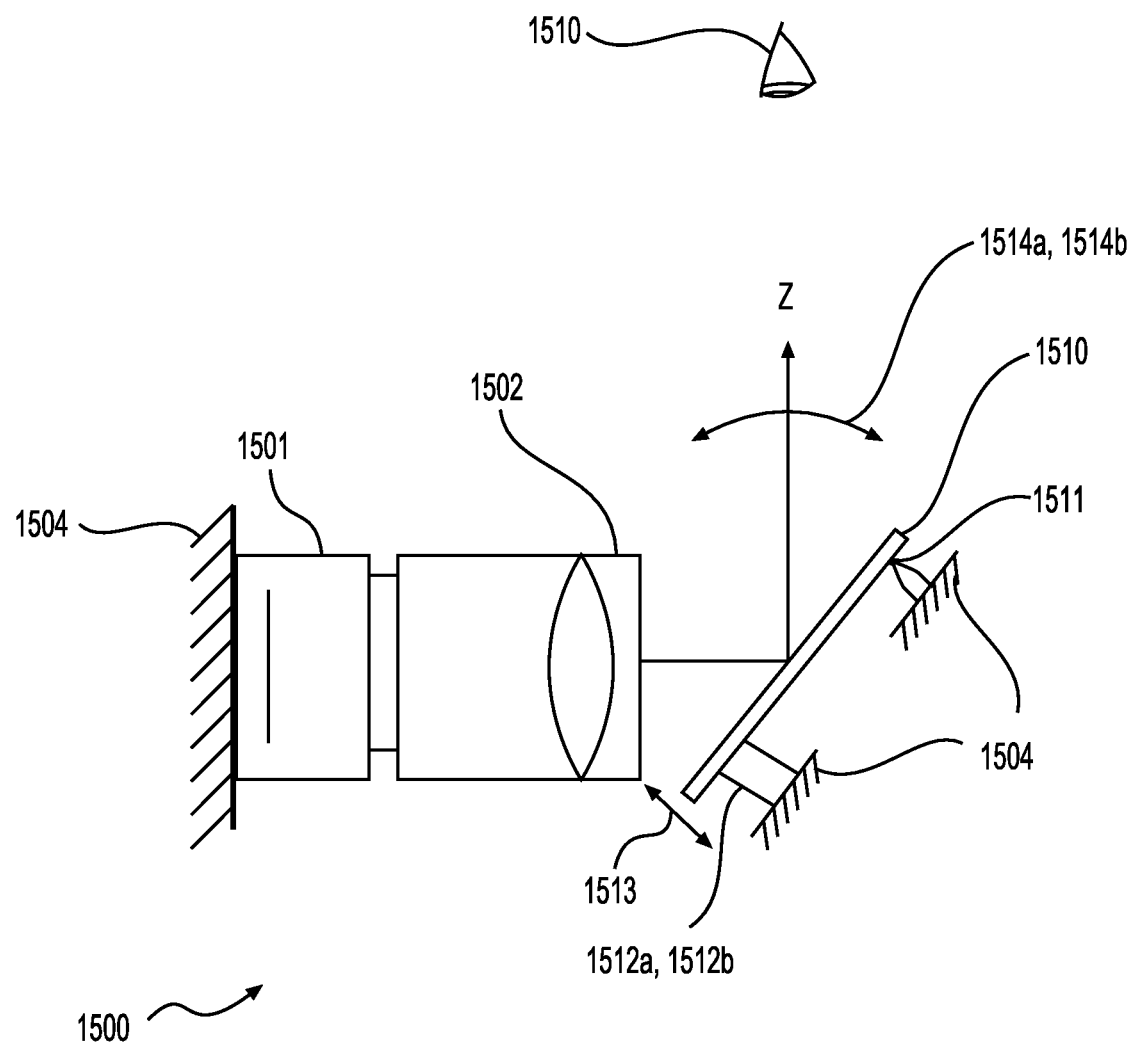
FIG. 15 illustrates an exemplary camera pan/tilt control mechanism with MEMS actuators used to control the viewing direction of the camera by controlling the pan and tilt angle of a mirror placed in front of the camera lens, in accordance with various embodiments.

FIG. 15 illustrates an embodiment 1500 of an eyefollower pan/tilt control mechanism employing MEMS devices to steer the pointing direction of the camera by rotating a mirror 1510 located in front of lens 1502, in accordance with various embodiments. In this example, camera body 1501 is attached to eyefollower chassis 1504 and camera lens 1502 is attached to camera body 1501. The position and angular orientation of rotatable mirror 1510 is determined by three (3) attachment points. First, a mirror pivot point 1511 attached to one point on the mirror is anchored to eyefollower chassis 1504. Second, a pair of linear MEMS actuators 1512a and 1512b, each with one end attached to eyefollower chassis 1504, are connected at their other ends to the second and third points on mirror 1510. The three (3) connection points are arranged in a triangular pattern such that the combined travels of actuators 1512a and 1512b result in mirror pan/tilt angles 1514a and 1514b required to reflect the camera's view direction Z toward eye 1510. In an embodiment, the nominal orientation of mirror 1510 is 45 degrees with respect to the camera longitudinal axis, and the nominal direction of the two actuator travels are approximately perpendicular to the mirror plane (as drawn in FIG. 15).

It should be noted that, in either the direct camera-control configuration of FIG. 14 or in the indirect mirror-control configuration of FIG. 15, the two actuators need not be configured to control the pan and tilt independently. As long as some combination of actuator positions provides access to all the desired pan and tilt orientations, any cross coupling between the control axes may be mathematically decoupled in the control algorithms implemented in the eyefollower's computer software. The use of decoupling in the control software allows significant freedom in the mechanical design of the actuator connection points, resulting in further miniaturization of the overall eyefollower package.

Focus Control

Figure 16:
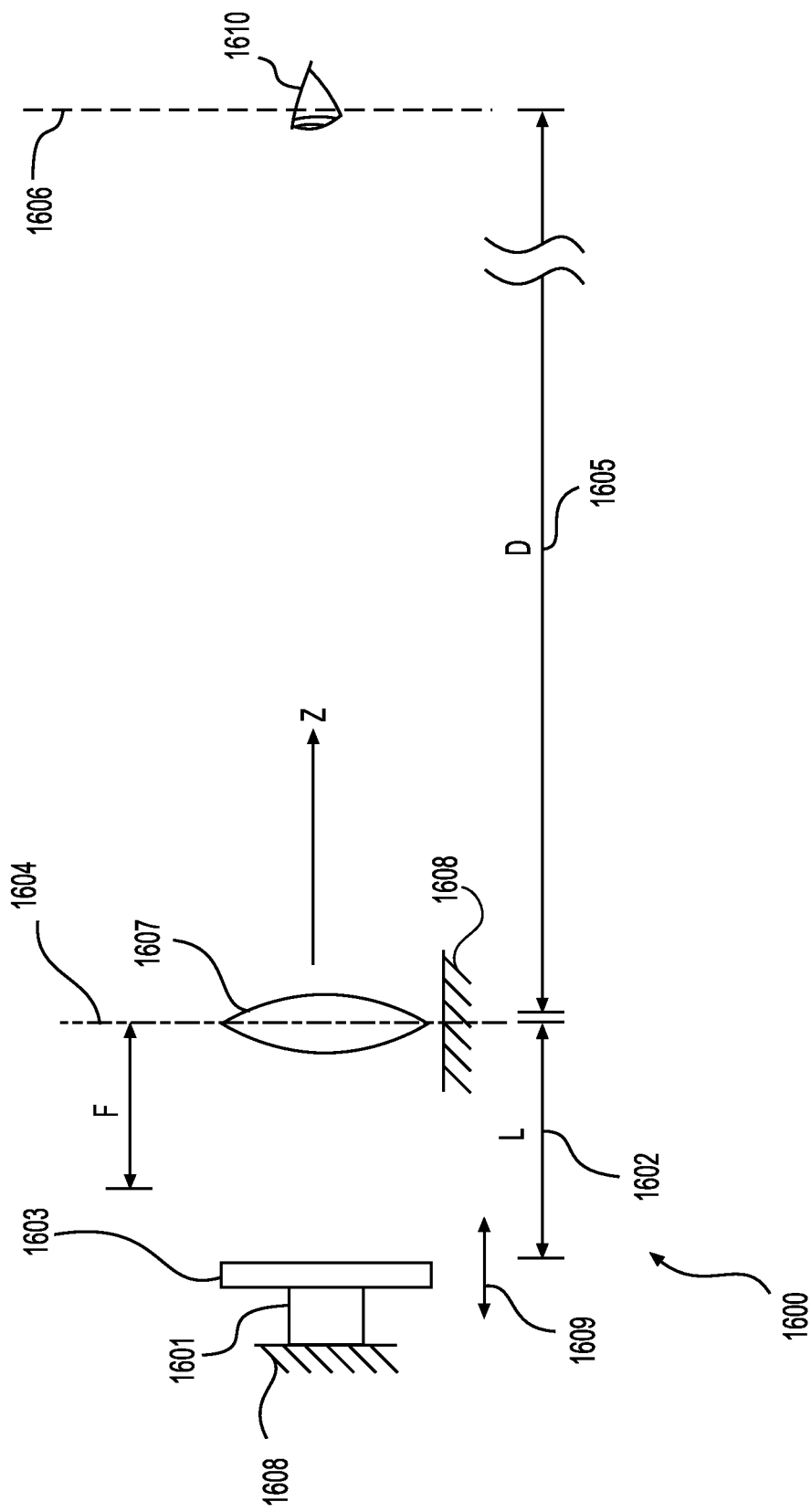
FIG. 16 illustrates an exemplary camera focus control mechanism with a MEMS actuator used to control the distance L between the camera lens plane and the camera image sensor, in turn providing control of the camera focus distance D, in accordance with various embodiments.

In various embodiments, MEMSs are also used to control the focus of an eye tracker camera to achieve desired focus conditions on the eye(s). FIG. 16 illustrates an exemplary camera focus control mechanism with a MEMS actuator used to control the distance L between the camera lens plane and the camera image sensor, in turn, providing control of the camera focus distance D, in accordance with various embodiments. For example, FIG. 16 shows a camera focus control system 1600 for a camera that has a conventional, rigid lens with fixed focal length F. An MEMS actuator 1601 controls an adjustable lens length L, 1602, between camera sensor 1603 and camera lens plane 1604, which in turn determines the focus distance D, 1605, from camera lens plane 1604 to camera focus plane 1606. In this embodiment, both camera lens 1607 and the rear end of linear actuator 1601 are attached to eyefollower chassis 1608, i.e., the eyefollower's fixed framework. The front end of linear actuator 1601 is attached to camera sensor 1603, and the actuator's direction of travel 1609 is along the camera's longitudinal axis Z, providing direct control of the camera lens length L, 1602, and ultimately allowing camera 1600 to focus on eye 1610.

Note that the key direct variable to control when focusing a camera with a fixed focal length is the lens length L, 1602, between camera sensor 1603 and camera lens plane 1604. In the focus-control embodiment of FIG. 16, camera lens 1607 is fixed to eyefollower chassis 1602 and camera sensor 1603 moves with linear actuator 1601. In a mechanically different but functionally equivalent implementation, sensor 1603 is directly attached the eyefollower chassis 1608, and the position of lens 1607 is controlled by actuator 1601.

As an alternative to a fixed-focal-length lens, an eye tracker camera may also employ a lens with variable focal length F. Variable-focal-length lenses include, for example, liquid, elastic and flexible lenses whose refractive powers are adjusted by physically modifying the shape of the lens. In various eye tracking embodiments, variable-focal-length lenses are also controlled by MEMS devices.

Figure 17A:
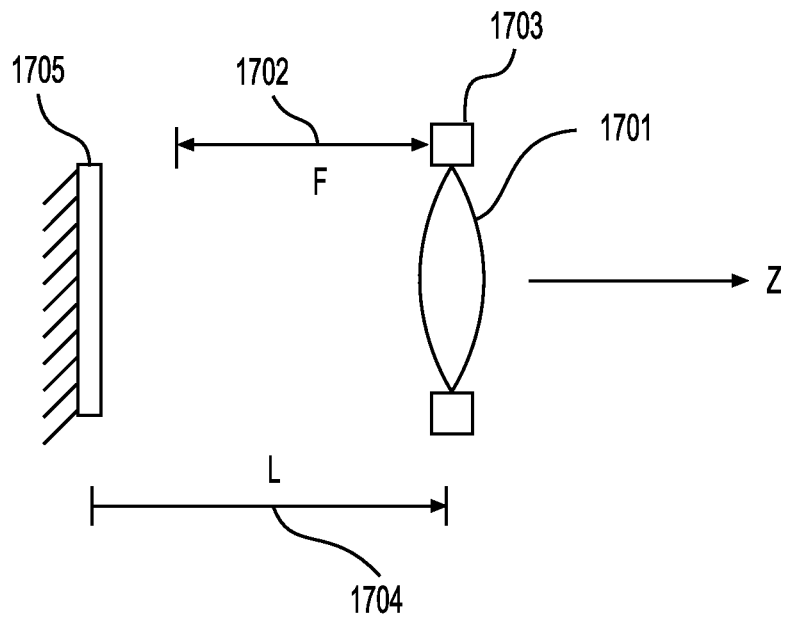
FIGS. 17A and 17B show an example camera focus control mechanism with a MEMS actuator used to control the focus power of a variable focus-power lens such as a liquid or elastic lens, in accordance with various embodiments.
Figure 17B:
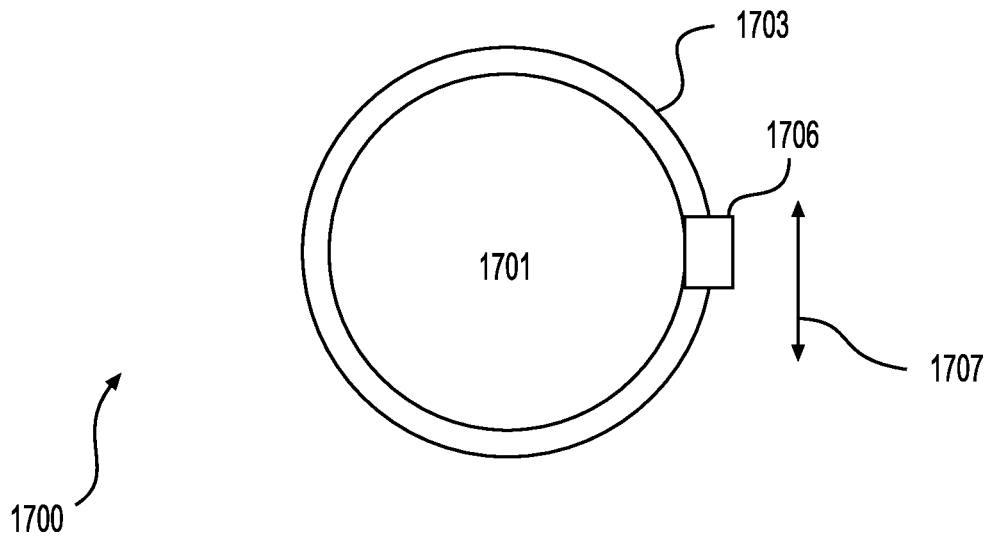

FIGS. 17A and 17B show an example of a camera 1700 with a variable-power lens 1701, whose variable focal length F, 1702, is controlled by a lens compression ring 1703 that squeezes the lens material to increase the focus power P and shorten the focal length F, in accordance with various embodiments. In this embodiment, the lens length L, 1704, between lens 1703 and sensor 1705 is constant, as illustrated in FIG. 17A. FIG. 17B shows a front view of lens 1701 with lens compression ring 1703 encircling the outer perimeter of the lens. A linear MEMS actuator 1706 inserted in an opening of lens compression ring 1703 causes the ring to expand or contract, in turn adjusting the power P of the lens.

Zoom Control

In various embodiments, MEMS may also be used to control the zoom of an eye tracker camera. As a user moves his head back and forth with respect to the camera's housing device, the zoom of the lens may be controlled to maintain a desired pixel resolution of the eye within the overall camera image.

Figure 18:
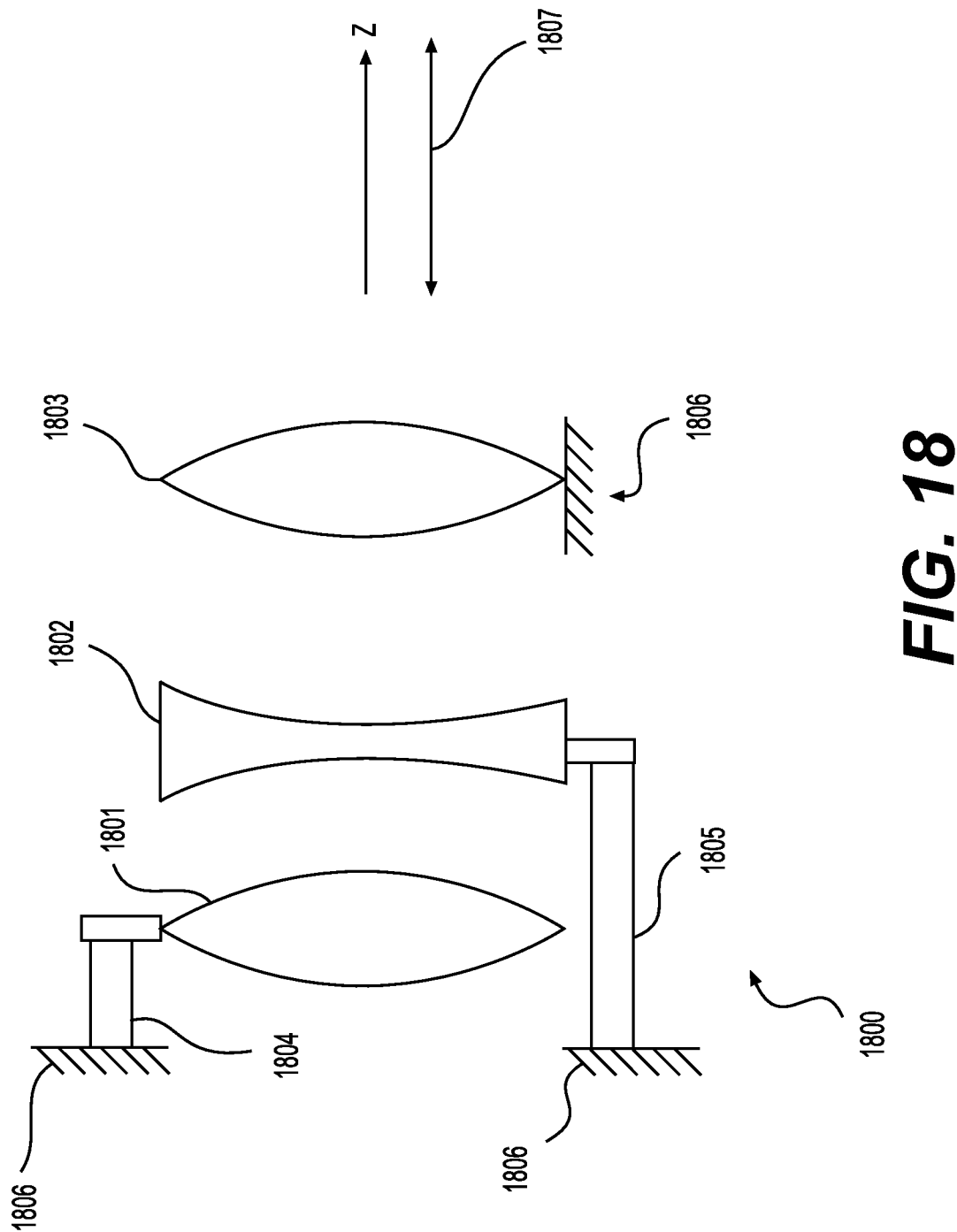
FIG. 18 illustrates an example of a lens with variable zoom, in accordance with various embodiments.

FIG. 18 illustrates an example of a lens 1800 with variable zoom, in accordance with various embodiments. The zoom function of the lens typically consists of the relative positioning of three (3) lenses: a convex lens element E1, 1801, a concave lens element E2, 1802, and another convex lens element E3, 1803. As illustrated in FIG. 18, lens element E3, 1803, is fixed with respect to lens housing 1806, and lens elements E1, 1801, and E2, 1802, move relative to E3 along the lens's longitudinal axis Z to achieve the variable zoom. The middle element E2, 1802, typically moves over the whole range between the outer elements E1, 1801, and E3, 1803. Element E1, 1801, typically moves over a much smaller range from its nominal position. Linear actuators 1804 and 1805 move the lens elements E1 and E2 respectively. To effect these element motions, linear actuators 1804 and 1805 are each connected at one end to lens housing 1806 and at the other end to their respective lens elements E1 and E2.

In various embodiments, a miniature eye tracking system includes a camera to image an eye, a microelectromechanical (MEMS) device to control the view-direction of the camera, and a processor. The processor receives an image of the eye from the camera, determines the location of the eye within the camera image, and controls the MEMS device to keep the camera pointed at the eye.

In various embodiments, the MEMS device controls a pan/tilt platform on which the camera is mounted.

In various embodiments, the MEMS devices are attached directly to the camera.

In various embodiments, the MEMS device controls a pan/tilt mirror to steer the camera view direction.

In various embodiments, the camera includes an open-center asymmetric aperture device that has a single transparent opening and a set of opaque intrusion areas. An outer perimeter of the single transparent opening is inscribed in a circle and the set of opaque intrusion areas intrude into the outer perimeter of the inscribed circle.

In various embodiments, a method is provided to control the view-direction of a camera using a microelectromechanical (MEMS) device. An image is received from camera using a processor. A location of the eye is determined within the image using the processor. A MEMS device is controlled to keep the camera pointed at the eye using the processor.

In various embodiments, a miniature eye tracking system includes a camera to image an eye, a microelectromechanical (MEMS) device to control an adjustable focus of the camera, and a processor. The processor receives an image of the eye from the camera, determines the focus condition of the eye image, and controls the MEMS device to maintain a desired focus condition of the camera on the eye.

In various embodiments, the camera's lens has a fixed focal length F, the camera's focus condition is controlled by adjusting the distance L between the lens plane and the camera sensor surface, and the MEMS device adjusts the distance L.

In various embodiments, the camera's lens has a variable focal length F, the camera's focus condition is controlled by adjusting the lens focal length F, and the MEMS device adjusts the lens focal length F.

In various embodiments, the camera includes an open-center asymmetric aperture device that has a single transparent opening and a set of opaque intrusion areas. An outer perimeter of the single transparent opening is inscribed in a circle and the set of opaque intrusion areas intrude into the outer perimeter of the inscribed circle.

In various embodiments, a method is provided to control an adjustable focus of the camera using a microelectromechanical (MEMS) device. An image is received from camera using a processor. A focus condition is determined from the image using the processor. A MEMS device is controlled maintain a desired focus condition of the camera on the eye using the processor.

In various embodiments, a miniature eye tracking system includes a camera to image an eye, a microelectromechanical (MEMS) device to control an adjustable camera zoom, and a processor. The processor receives an image of the eye from the camera, determines the size of the eye image within the overall camera image, and controls the MEMS to maintain a desired size of the eye image within the overall camera image.

In various embodiments, the camera includes an open-center asymmetric aperture device that has a single transparent opening and a set of opaque intrusion areas. An outer perimeter of the single transparent opening is inscribed in a circle and the set of opaque intrusion areas intrude into the outer perimeter of the inscribed circle.

In various embodiments, a method is provided to control an adjustable camera zoom using a microelectromechanical (MEMS) device. An image is received from camera using a processor. A size of an eye image within the image is determined using the processor. A MEMS device is controlled maintain a desired size of the eye within the image using the processor.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A miniature eye tracking system, comprising:
a camera to image an eye,
a microelectromechanical (MEMS) device to control the view-direction of the camera, and
a processor that
  receives an image of the eye from the camera,
  determines the location of the eye within the camera image, and
  controls the MEMS device to keep the camera pointed at the eye, wherein the camera includes an open-center asymmetric aperture device that has a single transparent opening and a set of opaque intrusion areas, wherein an outer perimeter of the single transparent opening is inscribed in a circle and the set of opaque intrusion areas intrude into the outer perimeter of the inscribed circle.

2. A miniature eye tracking system, comprising:
a camera to image an eye;
a microelectromechanical (MEMS) device to control an adjustable focus of the camera; and
a processor that
  receives an image of the eye from the camera,
  determines the focus condition of the eye image, and
  controls the MEMS device to maintain a desired focus condition of the camera on the eye, wherein:
  the camera's lens has a fixed focal length F,
  the camera's focus condition is controlled by adjusting the distance L between the lens plane and the camera sensor surface, and
  the MEMS device adjusts the distance L.

3. A miniature eye tracking system, comprising:
a camera to image an eye;
a microelectromechanical (MEMS) device to control an adjustable focus of the camera; and
a processor that
  receives an image of the eye from the camera,
  determines the focus condition of the eye image, and
  controls the MEMS device to maintain a desired focus condition of the camera on the eye, wherein:
  the camera's lens has a variable focal length F,
  the camera's focus condition is controlled by adjusting the lens focal length F, and
  the MEMS device adjusts the lens focal length F.

4. A miniature eye tracking system, comprising:
a camera to image an eye;
a microelectromechanical (MEMS) device to control an adjustable focus of the camera; and
a processor that
  receives an image of the eye from the camera,
  determines the focus condition of the eye image, and
  controls the MEMS device to maintain a desired focus condition of the camera on the eye, wherein the camera includes an open-center asymmetric aperture device that has a single transparent opening and a set of opaque intrusion areas, wherein an outer perimeter of the single transparent opening is inscribed in a circle and the set of opaque intrusion areas intrude into the outer perimeter of the inscribed circle.

5. A miniature eye tracking system, comprising:
a camera to image an eye;
a microelectromechanical (MEMS) device to control an adjustable camera zoom; and
a processor that
  receives an image of the eye from the camera,
  determines the size of the eye image within the overall camera image, and
  controls the MEMS to maintain a desired size of the eye image within the overall camera image, wherein the camera includes an open-center asymmetric aperture device that has a single transparent opening and a set of opaque intrusion areas, wherein an outer perimeter of the single transparent opening is inscribed in a circle and the set of opaque intrusion areas intrude into the outer perimeter of the inscribed circle.

* * * * *